United States Patent
Sherman et al.

[19]

[11] Patent Number: 5,891,159
[45] Date of Patent: Apr. 6, 1999

[54] AUTOMATIC PURSE STRING SUTURE DEVICE

[75] Inventors: Benjamin Sherman, Milpitas; Robert C. Glines, Cameron Park; Ivan Sepetka, Los Altos; Charles S. Taylor, San Francisco; Dwight P. Morejohn, Davis, all of Calif.

[73] Assignee: Cardiothoratic Systems, Inc., Cupertino, Calif.

[21] Appl. No.: 850,321

[22] Filed: May 2, 1997

[51] Int. Cl.⁶ ...................................................... A61B 17/04
[52] U.S. Cl. ............................................ 606/144; 606/139
[58] Field of Search .............................. 606/139, 144–148

[56] References Cited

U.S. PATENT DOCUMENTS

| | | | |
|---|---|---|---|
| 3,638,654 | 2/1972 | Akuba | 606/144 |
| 4,915,107 | 4/1990 | Rebuffat et al. | 606/144 |
| 5,171,257 | 12/1992 | Ferzli | 606/205 |
| 5,188,636 | 2/1993 | Fedotov | 606/144 |
| 5,242,457 | 9/1993 | Akopov et al. | 606/144 |
| 5,411,481 | 5/1995 | Allen et al. | 606/144 |
| 5,425,737 | 6/1995 | Burbank et al. | 606/144 |
| 5,490,856 | 2/1996 | Person et al. | 606/139 |

*Primary Examiner*—Gary Jackson
*Attorney, Agent, or Firm*—Lyon & Lyon LLP

[57] ABSTRACT

An automatic purse string suture device is disclosed that enables a surgeon to install a purse string suture in tissue structures, particularly for sealing the tissue about a cannula. The device is particularly suited for minimally invasive cardiothoracic procedures and is comprised of an applicator having an elongated structure with protrusions extending from the distal edge thereof. Also provided are means for advancing a needle through a passage to pass a suture through tissue that has been conformed to the distal edge of the device. Various means for conforming the tissue to the distal edge are disclosed as are methods for using the device to facilitate cardiothoracic surgery.

47 Claims, 17 Drawing Sheets

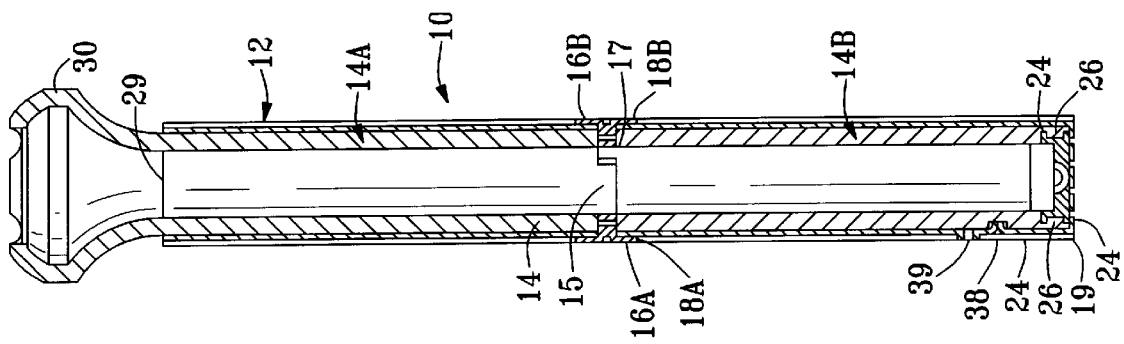
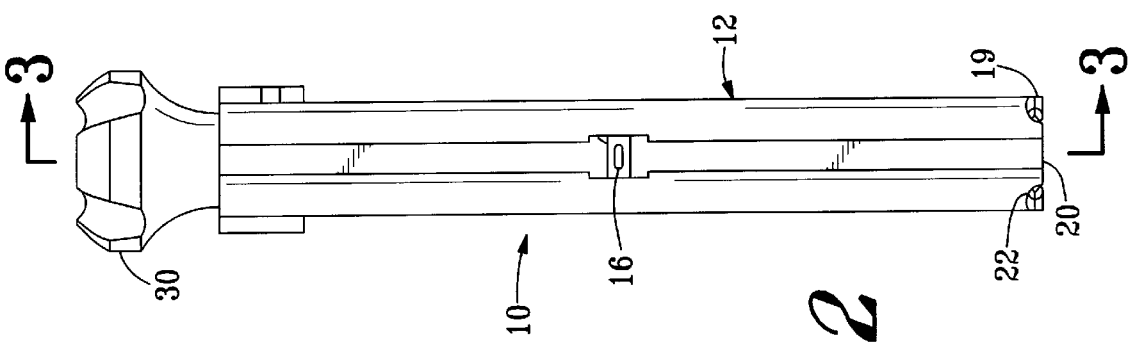

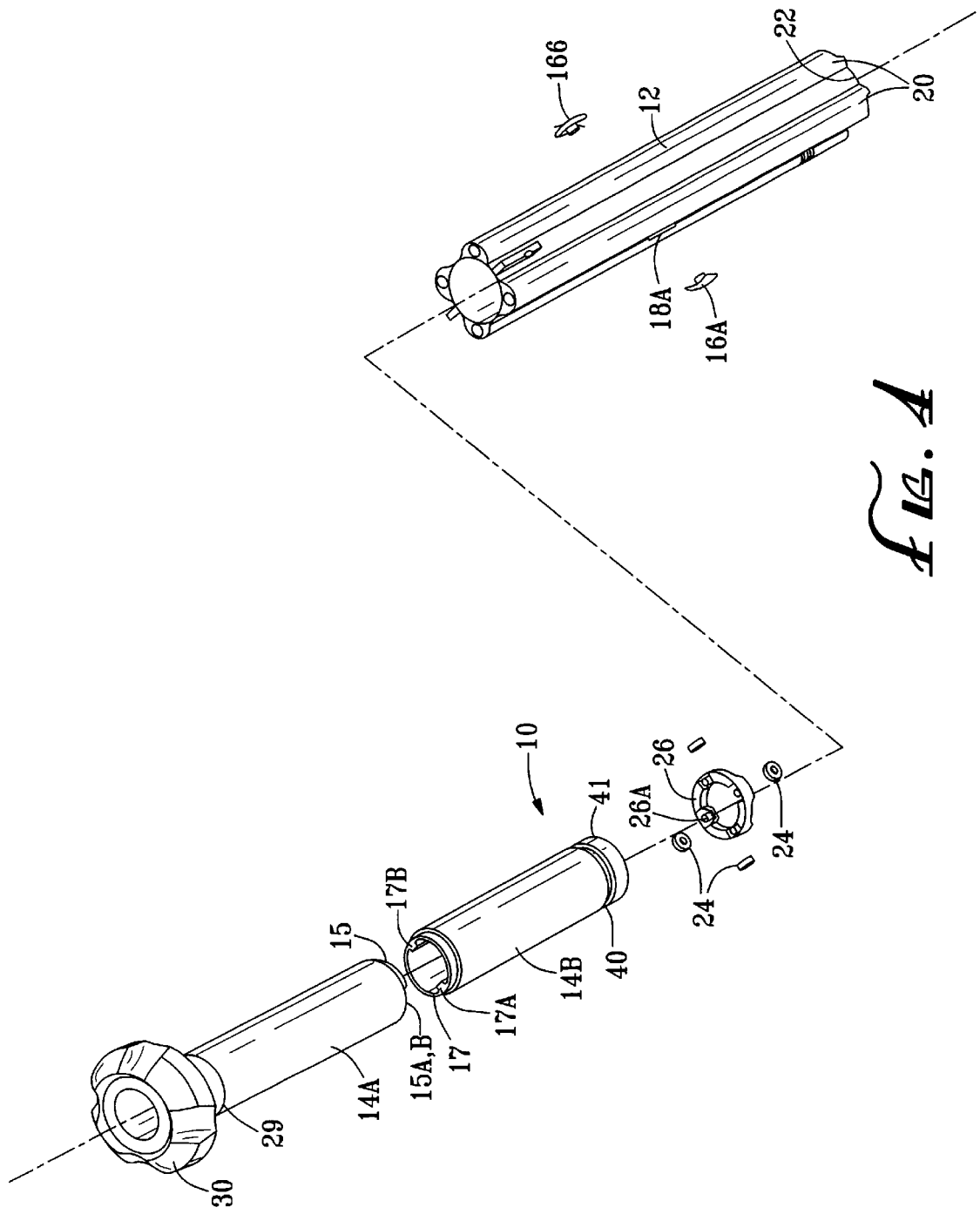

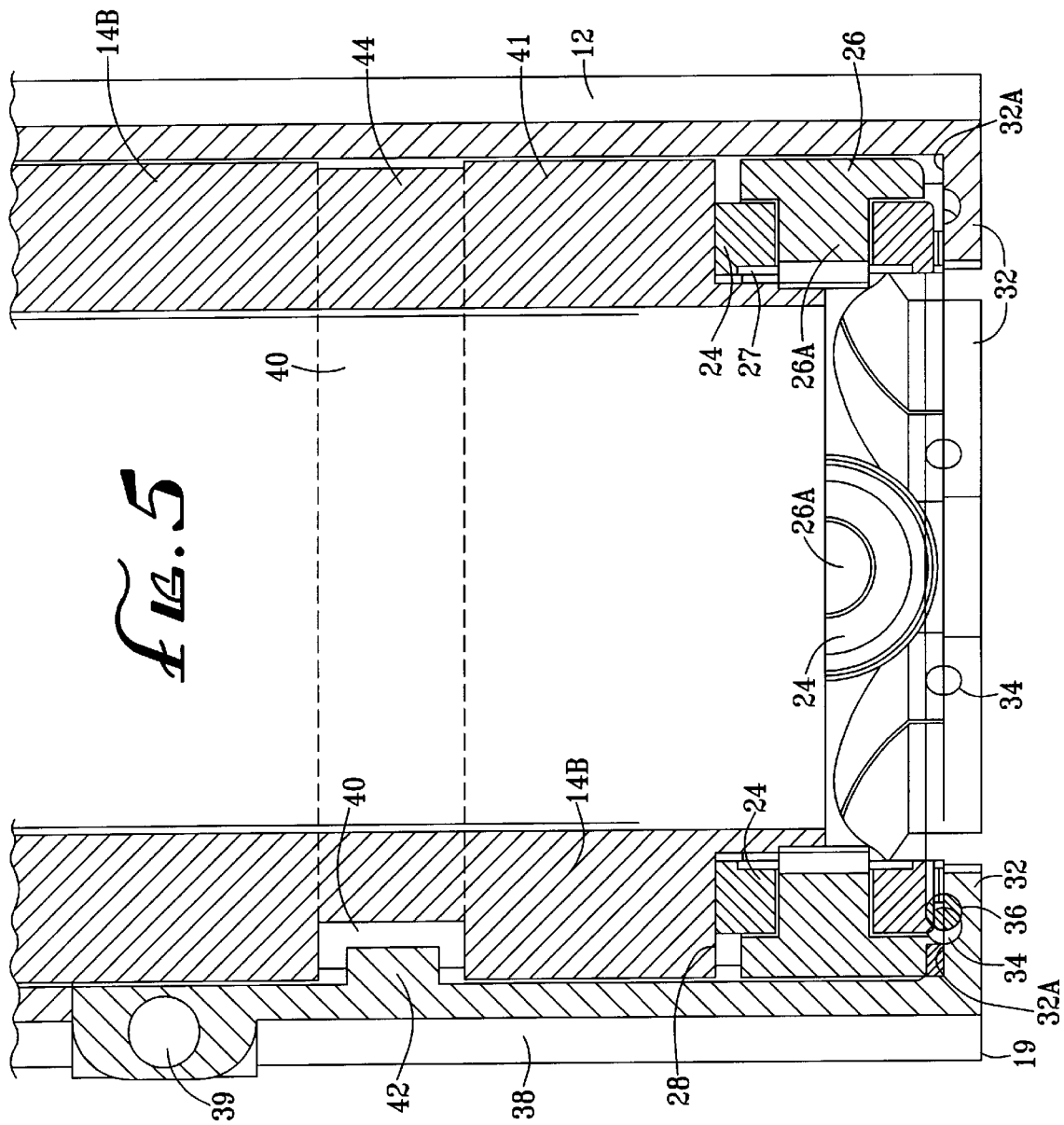

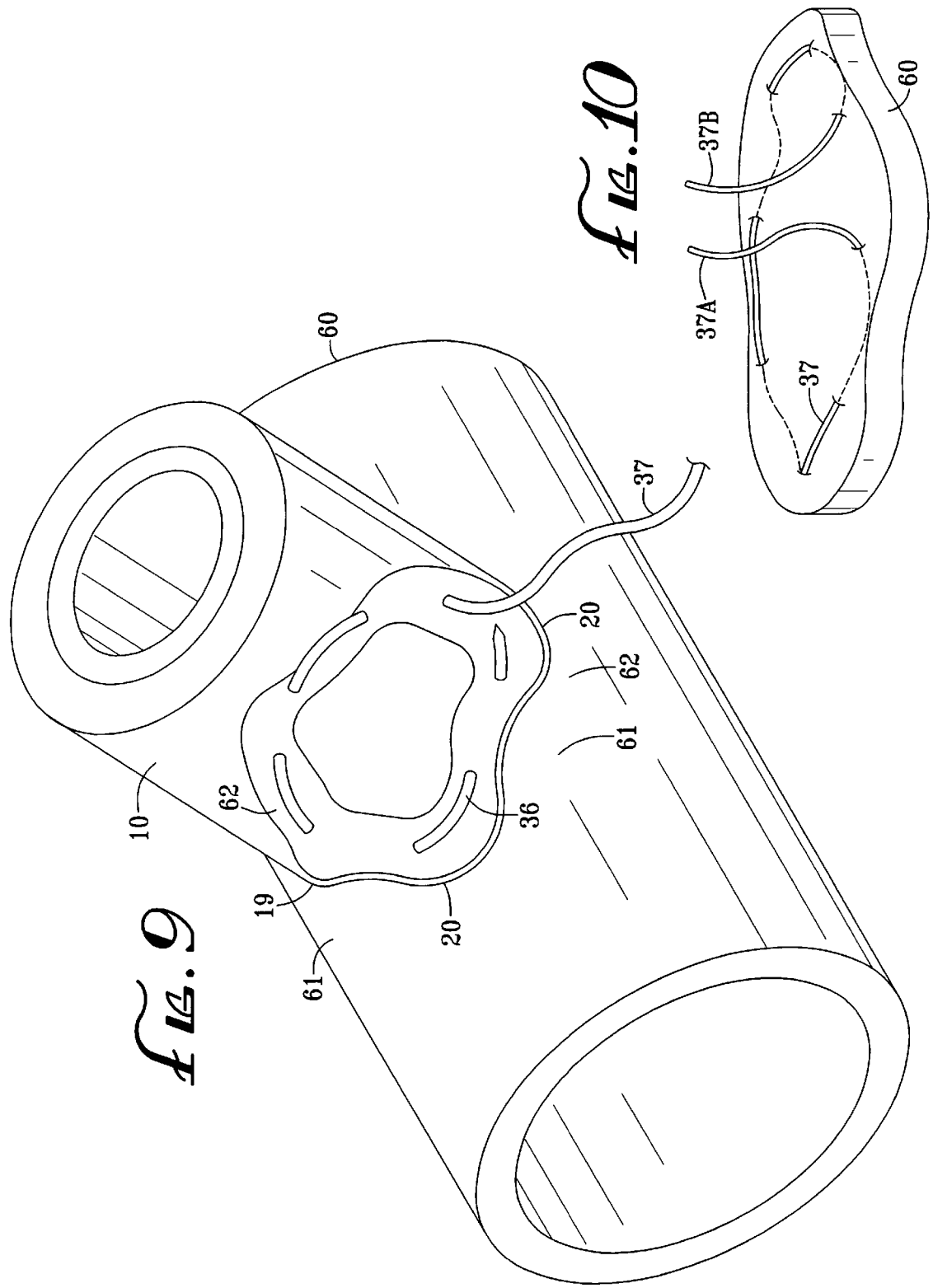

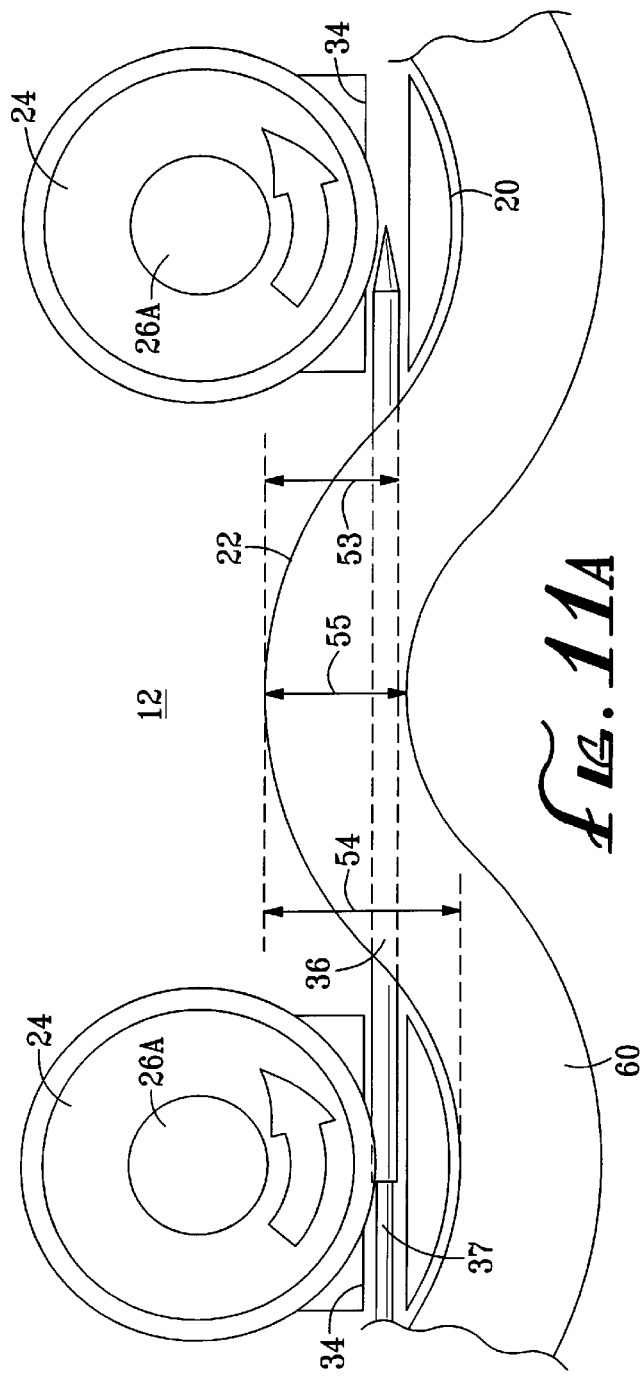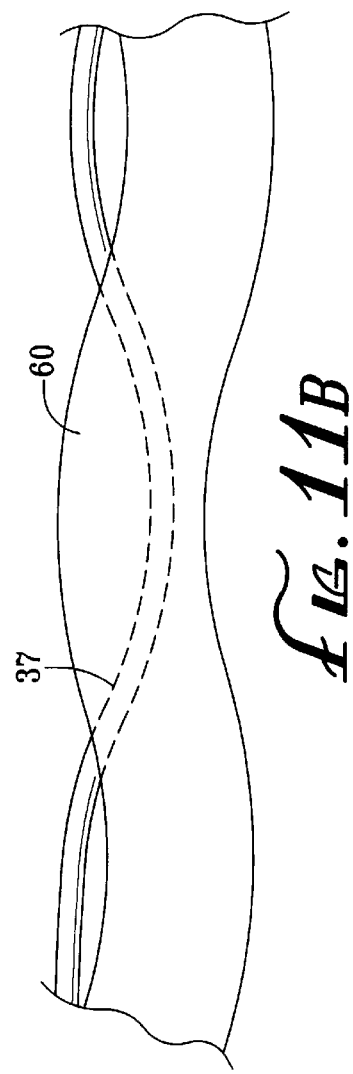

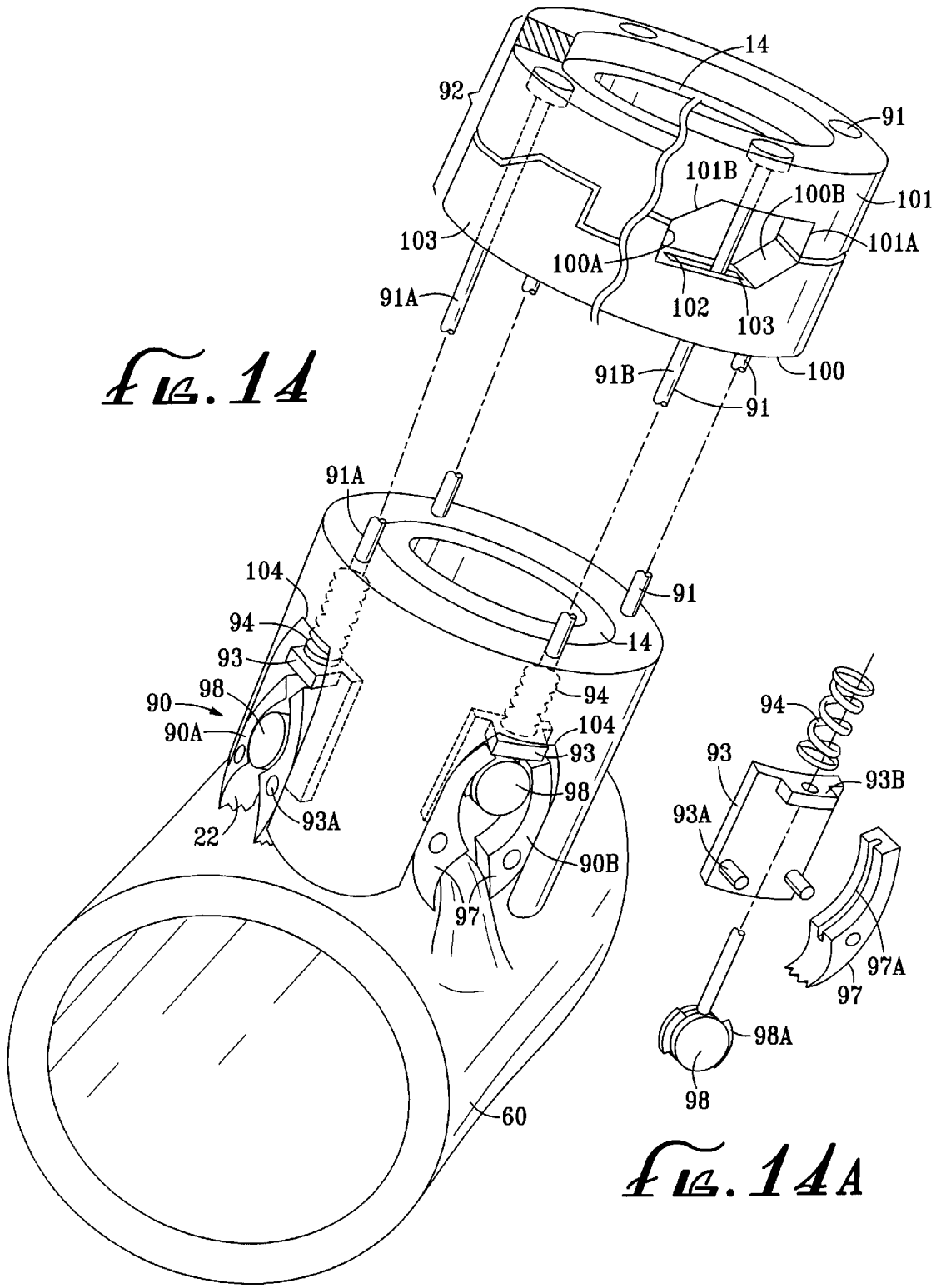

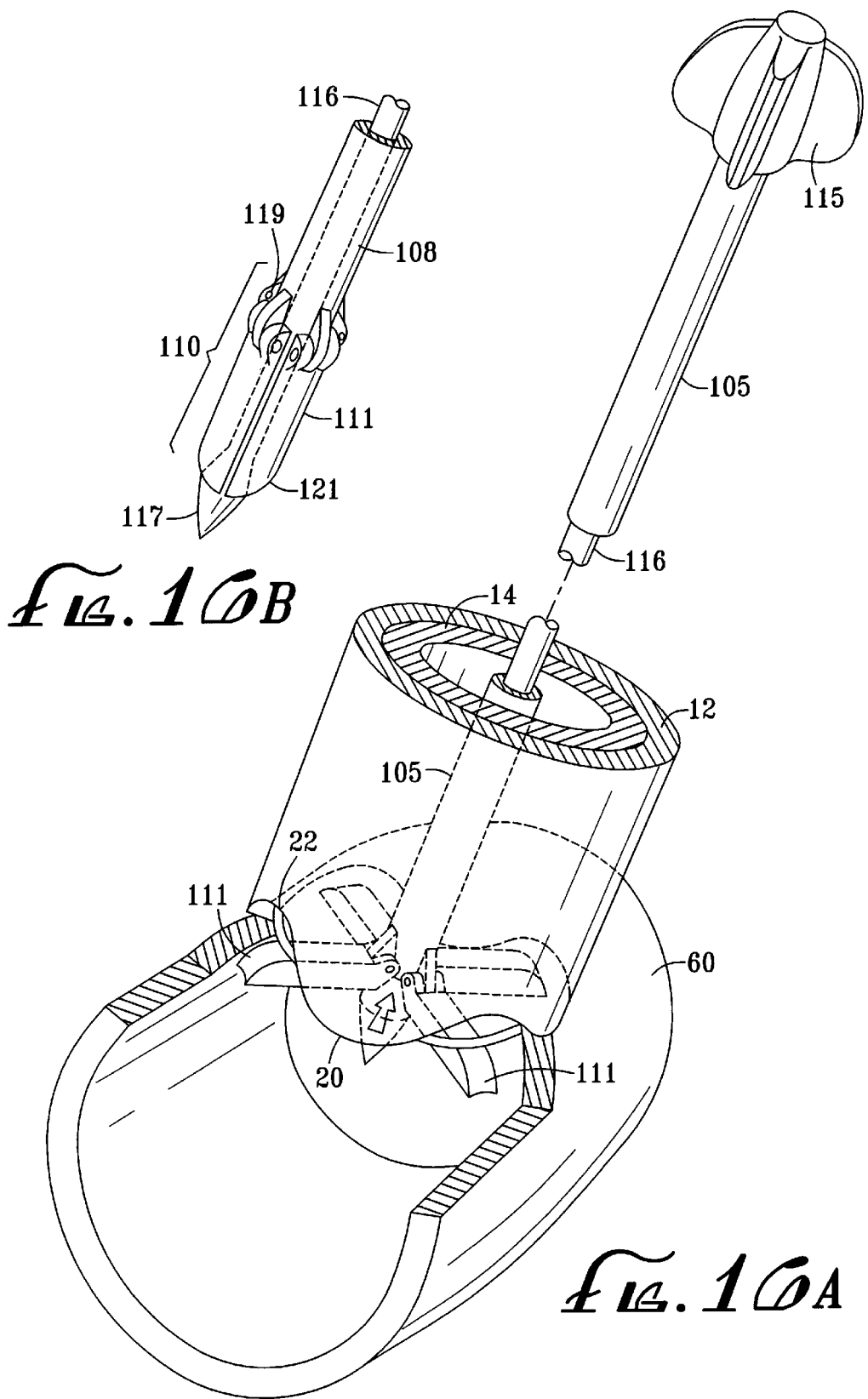

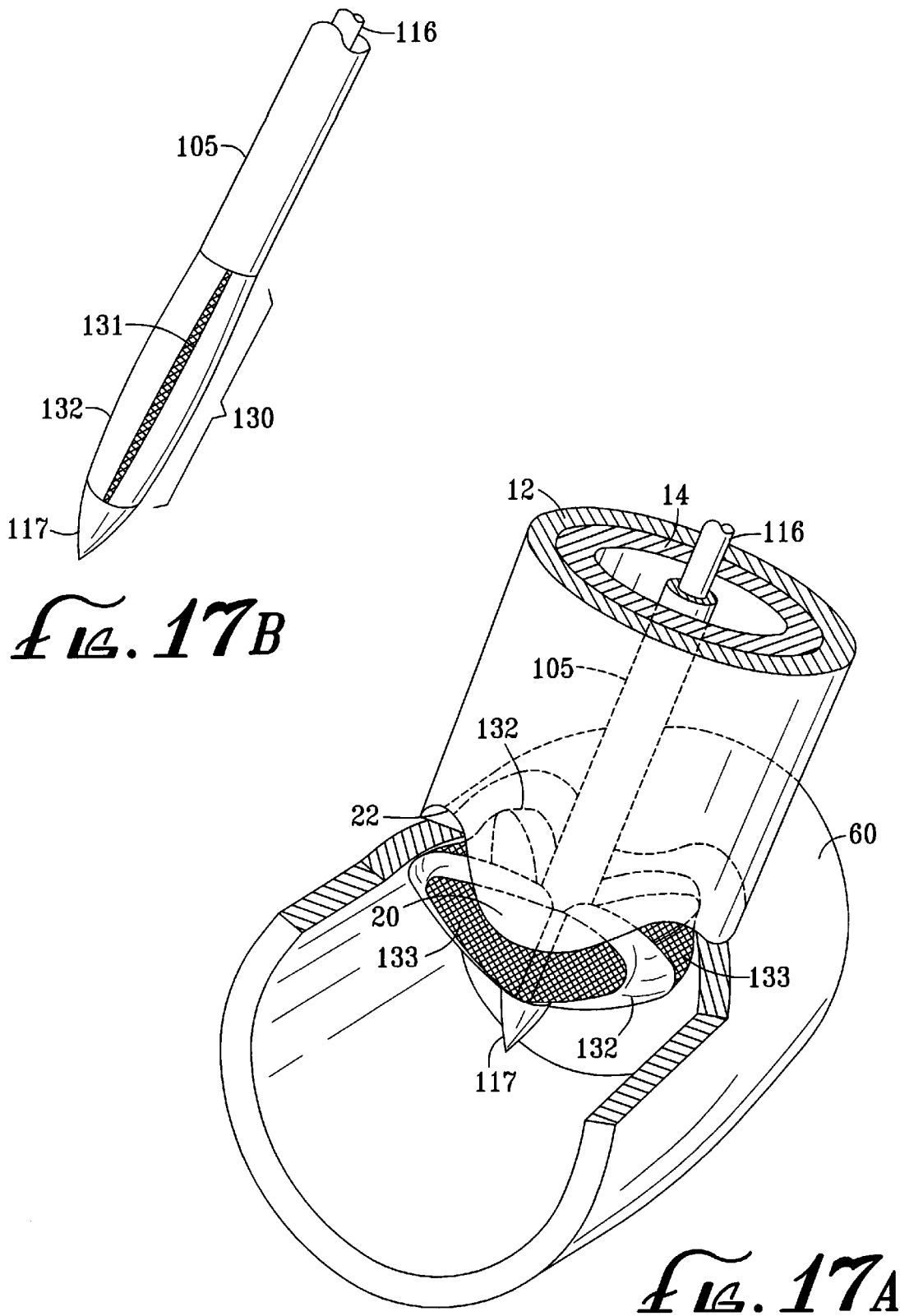

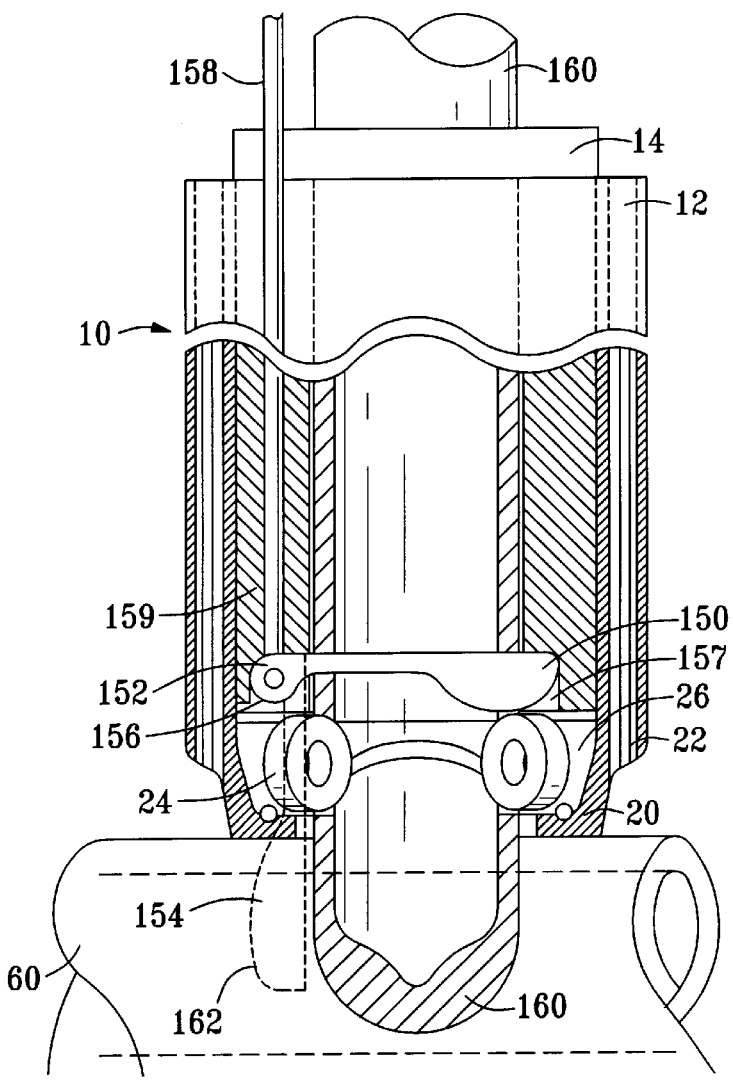
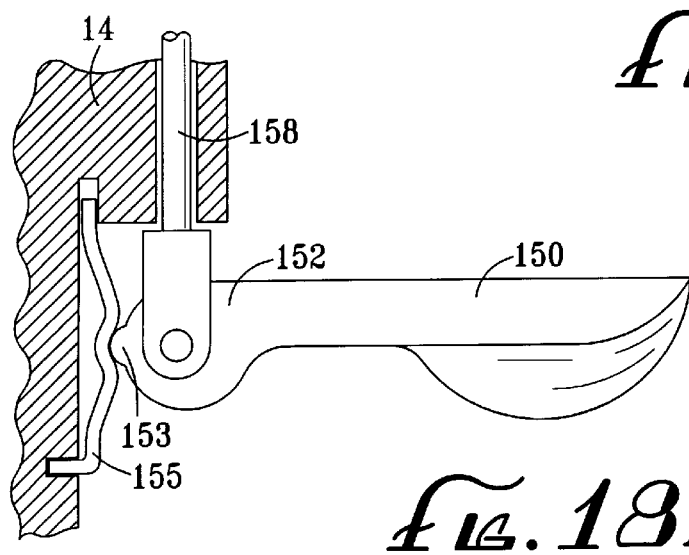
FIG. 18
FIG. 18A

AUTOMATIC PURSE STRING SUTURE DEVICE

FIELD OF THE INVENTION

The present invention generally relates to a surgical instrument for applying purse string sutures to tissue and, more particularly, to a surgical instrument for applying purse string sutures to a tissue vessel to be cannulated. Additionally, the present invention relates to a method for automatically applying purse string sutures to tissue.

BACKGROUND OF THE INVENTION

Purse string sutures are frequently used in surgical procedures to close a tubular section of tissue, e.g., intestinal tissue. Purse string sutures are also used in the performance of cardiac surgery wherein the heart, major arteries, and/or major veins are cannulated for cardiopulmonary bypass (CPB). More specifically, a purse string suture is used to seal the tissue around a cannula placed within the cardiac tissue.

Cardiopulmonary bypass requires a cannula (or cannulae) to be placed into the right side of the heart (typically the right atrium) or in the major veins (typically the superior vena cava and/or inferior vena cava) to drain blood from the patient and deliver it to a pump-oxygenator, commonly known as the heart-lung machine. In the pump-oxygenator, the blood is exposed to a gaseous mixture that eliminates carbon dioxide and adds oxygen to the blood. The oxygenated blood is then returned to the body through a perfusion cannula. In some circumstances, the perfusion cannula is placed into a large peripheral artery, such as the common femoral artery. However, because of a higher incidence of complications associated with that method of blood return to the body, it is more acceptable to return the blood through a cannula placed directly into the ascending aorta.

The insertion of the arterial (aortic) perfusion and the venous drainage cannula are usually performed in the following fashion. After the patient's chest has been opened and the pericardium (the protective sac around the heart) has been entered, two concentric purse string sutures are placed into the anterior wall of the ascending aorta just proximal to upstream of the brachiocephalic trunk. The diameter of the purse string suture is made large enough to accommodate the size of the aortic perfusion cannula. A "choker" tube or sleeve is positioned over the trailing ends of the suture threads to act as a tourniquet for tightening the purse string suture. A small incision is then made through the wall of the aorta into its lumen in the center of the purse-string sutures. The aortic perfusion cannula is then inserted through that incision into the aorta to prevent the escape of blood prior to connection to the pump-oxygenator. The purse string sutures are then tightened by means of their respective tourniquets to seal the aortic wall around the perfusion cannula in order to prevent the escape of blood from the aorta. Air is then evacuated from the perfusion cannula as it is joined by a connector to the tubing from the pump-oxygenator. A cross-clamp is placed on the aorta just downstream of the aortic root and upstream of the cannula to ensure that no blood flows back into the aorta during CPB.

The venous drainage cannula(e) is similarly inserted directly through an incision centered within a single purse-string suture into the right atrium of the heart or into the superior and/or inferior vena cavae for connection to the drainage side of the pump-oxygenator. The respective purse string sutures are tightened by means of a tourniquet as described above. An external clamp is sometimes placed around the vena cava to prevent blood from flowing between the vessel lumen and the venous cannula.

Cardiopulmonary bypass is instituted by allowing unoxygenated blood which is returning to the right side of the heart to be diverted into the pump-oxygenator where it is oxygenated and temperature-adjusted. From there, the blood is pumped into the patient's arterial system via the aortic perfusion cannula.

When it is desired to arrest cardiac function, a cardioplegic solution, such as potassium (KCl) is delivered to the myocardium by one or a combination of two general techniques, antigrade and retrograde. The infusion of cardioplegia fluid in an antegrade manner is accomplished by means of a cardioplegia cannula inserted at the aortic root wherein the fluid flows in the normal direction into the coronary ostia through the coronary arteries and into capillaries within the myocardium. Retrograde infusion of cardioplegia solution is directed into the right coronary sinus by means of a cardioplegia cannula inserted in the right atrium, and flows backwards into the coronary arteries and capillaries of the myocardium. With both techniques, a purse string suture may be used to seal the tissue around the cannula.

Typically, two concentric rows, with off-setting or staggered stitches and with each row having 4 to 5 stitches, are placed for the arterial perfusion cannula. Because the blood flow pressure is greater on the arterial side of the heart, a double purse string suture is used as a precaution in case one suture breaks. Two rows of stitches also help to minimizes the risk of blood leakage from the incision site. On the other hand, because there are not the pressure concerns on the venous side, only a single purse string suture having about 5 to 6 stitches is typically used for venous cannulation. As the cardioplegia camula is in a portion of the circulatory system that has been bypassed by CPB, there is virtually no concern of blood leakage, and only a single purse string suture is necessary to seal the tissue around the cannula and hold it in place.

The diameter of a purse string sutures is sized to accommodate the respective cannulae. Arterial cannulae range in size from about 8 French, having an inner diameter of about 0.10 inch or 2.5 mm (for pediatric use to) about 24 French, having an inner diameter of about 0.30 inch or 8.0 mm. Accordingly, the inner purse string suture for an arterial cannula has a diameter which is preferably slightly larger (about 3.2 mm or ⅛ inch) than that of the cannula, and the outer suture has a diameter which is also about 3.2 mm or ⅛ inch greater than the inner suture. As venous cannulae tend to be slightly larger than arterial cannulae to compensate for the slower flow of blood, their sizes typically range from about 12 French, having an inner diameter of about 0.15 inch or 4.0 mm, to about 40 French, having a diameter of about 0.52 inch or 13.2 mm. The diameter of the associated single purse string suture is then preferably about slightly larger (about 3.2 mm or ⅛ inch) than that of the venous cannula.

Conventionally, purse string sutures are manually stitched by the surgeon. In laparoscopic surgery, for example, where tubular ends of tissue are being tied off, the entire thickness of the tissue wall may be penetrated to achieve the desired suturing. However, in cardiac surgery, and particularly in the context of aortic cannulation, total penetration of the aortic wall by the purse string suture can cause catastrophic effects such as blood leakage, the introduction of air into the arterial system, and the disruption of calcified deposits from the innermost layer of the aortic wall. Additionally, penetration of the aortic wall by a needle or suture can damage the endothelial layer increasing the likelihood of the long-term buildup of stenotic deposits within the aorta. Thus, the surgeon must be cautious so as not to penetrate the entire thickness of the vessel wall. Uniform placement, spacing and length of the stitches are also important to minimize the risk that some of the stitches may rip away from the tissue when the ends of the purse string suture are pulled. With manual stitching, it is difficult to obtain uniform and accurate penetration of the purse string suture into the tissue. It is also difficult for a surgeon of average skill to obtain stitches which are uniform in length and evenly spaced apart.

Another drawback of applying purse string sutures manually is the space required in the surgical opening for the surgeon's hands. With the progression towards less invasive cardiac surgical techniques which permit the visualization and manipulation of surgical instruments through less invasive openings in the chest, there is a need for a compact surgical instrument which automatically places purse string sutures in tissue structures and obviates the need for space to view the stitching procedure and accommodate the surgeon's hands.

Another objective of less invasive surgeries is to reduce the time a patient is subjected to potentially traumatic procedures, such as the necessary clamping of the aorta prior to implementing CPB and thereby reduce the interruption in systemic circulation. Although some cardiac surgeon's are very skilled and adept at placing purse string sutures by hand, it takes about 3 to 5 minutes to apply each purse string suture. A total of 3 to 5 purse string sutures being placed for the entire cannulation procedure, manual stitching adds considerable time to the entire procedure.

There are several surgical instruments for applying purse string sutures about the periphery of tubular tissue without the need for a surgeon to manually insert the suture needles into the tissue. For example, U.S. Pat. Nos. 4,915,107, and 5,188,636 disclose instruments in the form of a pair of serrated tissue clamping jaws provided with teeth. Needle passages extend through the teeth on each jaw for receiving a needle attached to a suture to be threaded through the tissue. The tissue clamping jaws act to gather tissue into the spaces between the teeth and then the needles are advanced through the needle passages. Other instruments are disclosed, in U.S. Pat. Nos. 4,749,114, 4,821,939, 5,242,457 and 5,484,451 for example, which utilize a plurality of staples for applying purse string sutures to human tissue. U.S. Pat. No. 5,484,451 discloses a surgical stapler having a pair of jaws with each jaw containing a staple cartridge for holding staples. The staples are shaped to have an eyelet for receiving a purse string suture.

These aforementioned devices are adapted for the application of a purse string suture circumferentially about an end or the periphery of a tubular tissue structure. They are not practical for applying purse string sutures to a closed vessel or vessel lumen, such as the heart or aorta, where it is desirable to apply a suture to only one wall or side of the vessel or lumen rather than about its periphery. The clamping jaw mechanism of these devices is also undesirable for use in creating purse string sutures in cardiac tissue, and the aorta in particular, as they tend to be traumatic to the tissue, increasing the risk of embolism. Furthermore, these instruments are not suitable for applying a purse string suture where it is necessary to avoid penetrating the suture through the entire thickness of the tissue wall, such as in the aorta, or where the use of staples to secure a suture is less than desirable due to the increased risk of thrombosis and embolisms associated with stapling vascular tissue.

Accordingly, a general objective of the present invention is to provide a device and a method for automatically applying a purse string suture to a single wall of a vessel or vessel lumen which does so more accurately and in less time than manual suturing.

Another objective of the present invention is to provide an instrument for atraumatically providing a purse string suture which does not employ clamping jaws or staples.

It is also an objective of the present invention to provide a device which automatically applies a purse string suture to a tissue wall where the suture penetrates through less than the full thickness of the wall.

It is also an objective of the present invention to provide a surgical instrument for automatically applying a purse string suture to cardiac tissue which can be inserted through a relatively small opening in the chest, which does not necessitate viewing of the suturing site for achieving accurate results, and which occupies minimal space in the surgical opening.

Another object of the present invention is to provide an automatic purse string suture instrument which incorporates a cutting or puncturing element to incise the area within a purse string suture for placement of a cannula or cannulae.

Yet another object of the present invention is to provide an apparatus which applies two concentric purse string sutures simultaneously.

These and other objectives and advantages of the present invention will be more fully understood and appreciated by reference to the drawings and the following description of the invention.

SUMMARY OF THE INVENTION

The present invention involves devices and methods for automatically applying a purse string suture in the wall of a vessel lumen, comprising. Generally, one embodiment of the present invention provides an automatic purse string suture applicator which includes an elongated structure having a distal edge which has a plurality of spaced-apart protrusions. A needle passage is defined within the distal edge for retaining a surgical needle. Also provided is a means for advancing a needle through the needle passage, and means for releasably engaging the wall of a vessel lumen against said distal edge of said elongated structure. Preferably, the elongated structure is tubular and the needle passage is annular. In a preferred embodiment, the plurality of protrusions form a substantially sinusoidal pattern. In another preferred embodiment, the plurality of protrusions form a substantially castellated pattern. There may be any number of protrusions. However, for suturing cardiac tissue for purposes of cannulation, four to six protrusions are preferable.

In one aspect of a preferred embodiment, the distance between the distal side of the needle passage and the distal edge of the structure at the midpoint between adjacent protrusions is less than the thickness of the vessel lumen wall. This configuration ensures that the needle is not driven through the entire thickness of the vessel wall, which in some cases, such as in the aorta, is essential.

The means for advancing an annular needle through the annular needle passage includes a plurality of rotatable disks integrally mounted within said tubular structure. The disks are mounted such that their circumferential surfaces are tangentially aligned with the needle passage such that rotation of the disks advances an annular needle through said annular passage. In turn, the disks are rotated by means proximally positioned outside of the thoracic cavity.

The purse string suture applicator of the present invention also provides various means for conforming the targeted tissue to the contoured distal edge of the tubular structure. Such means includes suction or grasping means integral with the tubular structure which are adapted to function completely external to the vessel lumen. Alternately, the conforming means may include a deployable or expandable mechanism, such as a balloon, braided sheath, or deployable support members which are inserted into the tissue structure or lumen in a deflated, retracted, or closed position and then inflated, expanded, or deployed to compress the tissue wall against the distal edge of the tubular structure.

Other aspects of the present invention include means for removing an annular needle from the annular needle passage after the needle has been advanced through the tissue wall. A cutting mechanism, such as a blade, for cutting an incision in the tissue wall for entry of a cannula and the like may also be provided. Additionally, an embodiment which places simultaneously places two concentric rows of purse string sutures is also provided.

Generally, the method of the present invention involves automatically applying a purse string suture in the wall of a tissue structure by first shaping the tissue wall into a substantially sinusoidal configuration having peak sections and valley sections, and then passing an annular needle having a suture attached thereto in an annular path through the peak sections of tissue.

A more particular method of automatically providing a purse string suture at a target site within the wall of a tissue structure includes providing an annular structure having a distal edge having a substantially sinusoidal configuration and engaging the distal edge against the target site. While the tissue wall at the target site is then conformed to the substantially sinusoidal configuration, an annular needle is caused to pass through the tissue wall.

BRIEF DESCRIPTION OF THE DRAWINGS

FIG. 2 is a side elevational side view of a tubular structure of an automatic purse string suture applicator of the present invention.

FIG. 3 is a longitudinal sectional view of the tubular structure taken along line 3—3 of FIG. 2.

FIG. 4 is an exploded view of the tubular structure illustrated in FIG. 2.

FIG. 5 is an enlarged illustration of the distal end of the tubular structure shown in FIG. 3.

FIG. 9 is a schematic illustration of a tubular structure operatively positioned to apply a purse string suture to a vessel lumen with its wall compressed against the distal edge of the tubular structure in preferably sinusoidal configuration and a needle with an attached suture thread partially advanced through its annular route.

FIG. 10 shows a cut-away portion of the tissue wall of FIG. 9 having a purse string suture provided in the wall.

FIG. 11A is a schematic illustration of a needle being advanced through a segment of a vessel wall by needle advancing disks of an automatic purse string suture applicator of the present invention, wherein the needle extends through less the than the entire thickness of the tissue wall.

FIG. 11B is a schematic illustration of the tissue wall segment of FIG. 11A having a suture thread therein which passes through less than the entire thickness of the tissue wall.

FIG. 14 is a schematic illustration of a purse string suture applicator of the present invention employing a gripper-type means for capturing tissue within the tissue bays of the tubular structure.

FIG. 14A shows the components of the gripper means of FIG. 14.

FIG. 16A is schematic representation of another embodiment of the tissue conforming means of the present invention in an active or open position. This embodiment employs an umbrella-like deployment mechanism having a plurality of support members.

FIG. 16B shows the distal end of the tissue compressing device of FIG. 16A when in a closed position. The tip of the distal end is also configured to have a trocar-like pointed tip for puncturing tissue.

FIG. 17A is yet another embodiment of the tissue conforming means of the present invention utilizing an expandable braided sheath, shown here in an open state.

FIG. 17B shows the distal end of the device of FIG. 17A in a closed position.

FIG. 18 shows a cross-section of an embodiment of the present invention employing a blade mechanism to incise the tissue wall for placement of a cannula.

FIG. 18A shows an enlarged view of the blade mechanism of FIG. 18A.

DETAILED DESCRIPTION OF THE INVENTION

Various preferred and exemplary embodiments of the automatic purse string suture applicator of the present invention are now described in more detail with reference to the Figures. The same reference numbers used throughout the Figures reference like elements or components of the invention. For purposes of this description, the present invention is described in the context of the application of purse string sutures to the coronary vasculature for purposes of cannulation. This application is intended to be exemplary and not limiting, and those skilled in the relevant arts and technologies will appreciate that the present invention has other surgical applications.

Figure 1:
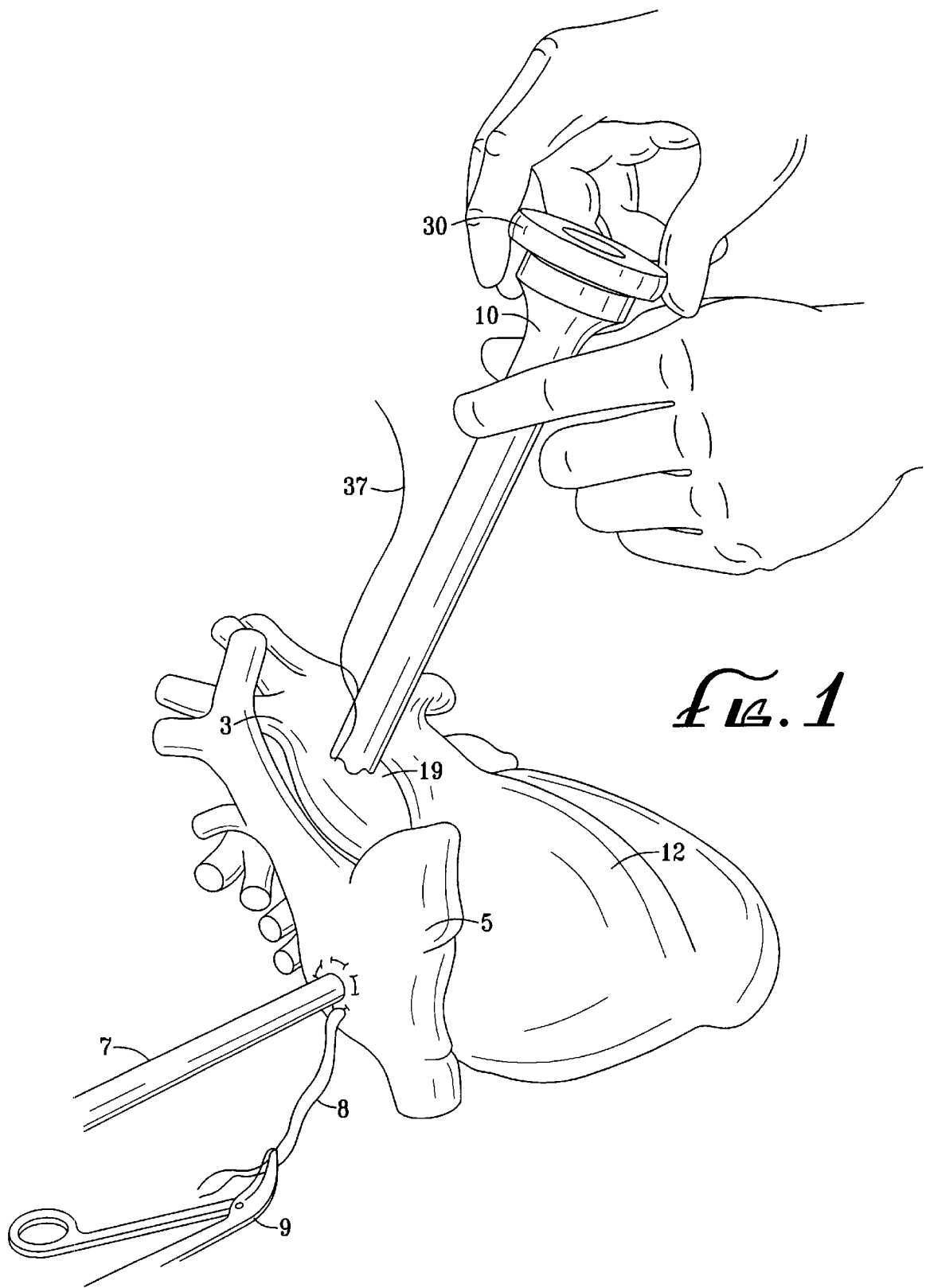
FIG. 1 is a schematic representation of the heart and various vasculature showing an automatic purse string suture applicator of the present invention operatively positioned to apply a purse string suture to cardiac tissue.

Referring first to FIG. 1, a schematic representation is provided of a heart 2 with various arterial and venous vasculature, and shows a elongated structure or body or structure 10 of the purse string suture applicator of the present invention operatively positioned for automatically applying a purse string suture to a vessel lumen or hollow tissue structure 3 which, in FIG. 1, is the aorta. The purse string suture applicator is "automatic" in that it eliminates the manual application of sutures to the tissue, and quickly and accurately applies a suture to tissue with minimal steps and in less time than manual suturing.

Generally, structure 10 is designed to have dimensions and a shape to be easily inserted through a surgical opening in the chest, including minimally invasive openings or delivered to the target site via a trocar sheath. Preferably, elongated structure 10 is a tubular housing but may have other configurations, such as a rectangular shape, and may also be a rod having a distal end having a selected configuration for passing a needle through a defined passage. The distal edge 19 of structure 10 has a contoured surface for contacting the tissue to be sutured. Preferably, the contoured surface is castellated or substantially sinusoidal, but may be configured of spaced-apart triangular, rectangular, circular, hexagonal, or other shaped protrusions. A needle passage (not shown) is defined within the distal end for holding an needle (also not shown) having a suture thread 37 attached. A needle driving means, such as a knob 39 at the proximal end of tubular structure 10, is employed to advance the needle through the passage.

The present invention also provides various means, which are not shown in FIG. 1, for conforming the targeted tissue to the contoured distal edge 19. In the various embodiments of the present invention, the means for conforming the tissue may include suction or grasping means integral with tubular structure 10 and are adapted to function completely external to the vessel lumen. Alternately, the conforming means may include a deployable or expandable mechanism, such as a balloon, braided sheath, or deployable support members which are inserted into the tissue structure or lumen in a deflated, retracted, or closed position and then inflated, expanded, or deployed to compress the tissue wall against the distal edge of the elongated tubular structure 10.

In general, the application of a suture using the present invention involves contacting the contoured distal edge 19 of an elongated structure or body or housing 10 at the target tissue site and then conforming the adjacent tissue to the contoured distal edge 19. Various means for conforming the tissue to the distal edge 19 are contemplated and are described in detail below. While the tissue is compressed against distal edge 19, the annular surgical needle (not shown) and attached suture thread 37, which are held within the needle passage, which is preferably annular, are caused to pass through the conformed tissue. The term "annular" as used herein means a ring or circle or portion thereof. Advancing the needle is accomplished in the embodiment shown by manually rotating knob 30. Upon complete rotation of the needle, the needle and attached end of the suture 37 are removed from the tubular structure 10, either by passive or active disengagement means, the various embodiments of which are also described in detail below. The tubular structure 10 is then removed from the surgical site. Next, the needle is cut from the suture thread 37 and a choker 8 may then be applied over the trailing ends of the suture thread. Forceps or a hemostat 9 may be used to hold the choker 8 in place.

If using an embodiment of the present invention having a tissue conforming means which is not inserted into the vessel lumen being cannulated, a cannula entry site is formed after placement of a purse string suture by cutting or puncturing the area of tissue defined by the purse string suture. For example, such a purse string suture 6 has been applied in the wall of the right atrium 5 in FIG. 1. In embodiments which employ an internally inserted means for compressing the tissue, the cannula entry site is necessarily formed prior to providing a purse string suture. A cannula, such as the venous cannula 7, is placed within the respective tissue structure or lumen, and the purse suture 6 is tightened by means of choker 8.

The remainder of this description provides a more detailed explanation of various embodiments of the purse string suture of the present invention and its components. In FIGS. 2–4, there is shown one embodiment of a tubular structure 10 which houses some of the components of the purse string suture applicator. Tubular structure 10 includes an outer tubular member 12 and an inner tubular member 14 both of which are preferably made of plastic. Outer tubular member 12 is preferably long enough to extend through a surgical opening, such as in the chest, and reach the surface of the vessel, organ, or other tissue structure or lumen to which a purse string suture is to be applied. Accordingly, outer tubular member 12 preferably has a length from about 8 to about 15 cm (3 to 6 inches). The center-to-center diameter of the annular needle passage (not shown) of outer tubular member 12 defines the diameter of the purse string suture to be applied. Thus, in the application of a purse string suture to a major artery to accommodate an arterial perfusion cannula, it is preferable that the center-to-center diameter of the annular needle passage outer tubular member 12 be about 3 mm greater than that of the arterial cannula. For example, for a 20 French arterial cannula (a common size for an arterial cannula), the center-to-center diameter of the annular needle passage defined in outer tubular member is approximately 10 mm and 13 mm for the inner and outer purse string sutures, respectively. As a typical size for a venous cannula is about 32 French, the diameter of the associated purse string suture for a venous cannula application is approximately 13.5 mm, or about that of the outer arterial purse string suture. However, it should be understood that the particular length and diameter dimensions of outer tubular member 12 will vary depending on the surgical application (arterial, venous, or cardioplegia cannulation) and individual patient anatomy.

The distal edge 19 of outer tubular member 12 is configured so as to have distally-extending, spaced-apart or staggered extended sections or protrusions 20. Preferably, extended sections 20 are evenly spaced-apart and have uniform dimensions. In the context of a suturing procedure, sections or protrusions 20 contact the tissue to be sutured upon insertion of outer tubular member 12 through a surgical opening, for example, in the chest. The configuration of distal edge 19 is designed such that when the tissue between protrusions 20 are caused to engage the portions of distal edge 19 between protrusions 20, referred to as tissue "bays" 22, the tissue is conformed to a wavy or sinusoidal configuration. For example, in the embodiment shown in FIGS. 2–7, distal edge 19 forms a substantially castellated configuration or pattern having extended sections 20 and spaces or bays 22. Alternately, distal edge 19 may have sections 20 which are rounded to form a sinusoidal configuration, as shown in FIGS. 1 and 8, such that sections 20 may be defined as "crests" or "peaks," and bays 22 there between may be defined as "troughs" or "valleys."

The number of sections 20 is application-specific. Preferably, for use in cannulation procedures in cardiac tissue, outer tubular member 12 has four, five or six extending sections or protrusions 20. More particularly, in one embodiment, outer tubular member 12 preferably has four or five protrusions 20 for applying a purse string suture (both inner and outer sutures) to a major artery such as the aorta. In an embodiment for applying a purse string suture to a major vein, such as the vena cavae, or the atrial wall, outer tubular member 12 preferably has five or six protrusions 20. However, it should be understood that, depending on the surgical application, outer tubular member 12 may have more or less protrusions 20, such as two, three, seven, eight, nine, ten, eleven or more.

Inner tubular member 14 may be a single housing structure, or have multiple tubular sections to incorporate certain limitations in the advancement or rotation of inner tubular member 14 with respect to outer tubular member 12. For example, referring to FIGS. 3 and 4, inner tubular member 14 is shown to have two sections, an upper or proximal section 14a and a lower or distal section 14b. Inner tubular member 14, and each of sections 14a and 14b are dimensioned to be rotationally and longitudinally engagable within outer tubular member 12. The proximal end 17 of lower section 14b and the distal end 15 of upper section 14a are configured with a mating configuration which prevents rotational movement of sections 14a and 14b relative to each other. In the embodiment illustrated, distal end 15 of upper section 14a has an extending inner wall having opposing openings 15a and 15b. Proximal end 17 of lower section 14b has an extending inner wall having opposing flanges 17a and 17b which matingly engage with opposing openings 15a and 15b, respectively. A retainer or stopper mechanism 16 is provided in the wall of outer tubular member 12 to retain or prevent proximal section 14a from extending or traveling axially downward or distally within outer tubular member 12 beyond a selected point, and likewise, maintains distal section 14b from traveling upwards or proximally. Retainer 16 includes two oppositely positioned retainer plugs 16a and 16b which, when inserted into respective holes 18a and 18b in the wall of outer tubular member 12, are flush with the outer wall and extend internally to reside in an annular groove at the distal end 15 of upper section 14a. The distal end 17 of upper section 14a is configured to fit within lower section 14b when both sections are operatively positioned within outer tubular member 12.

Figure 6:
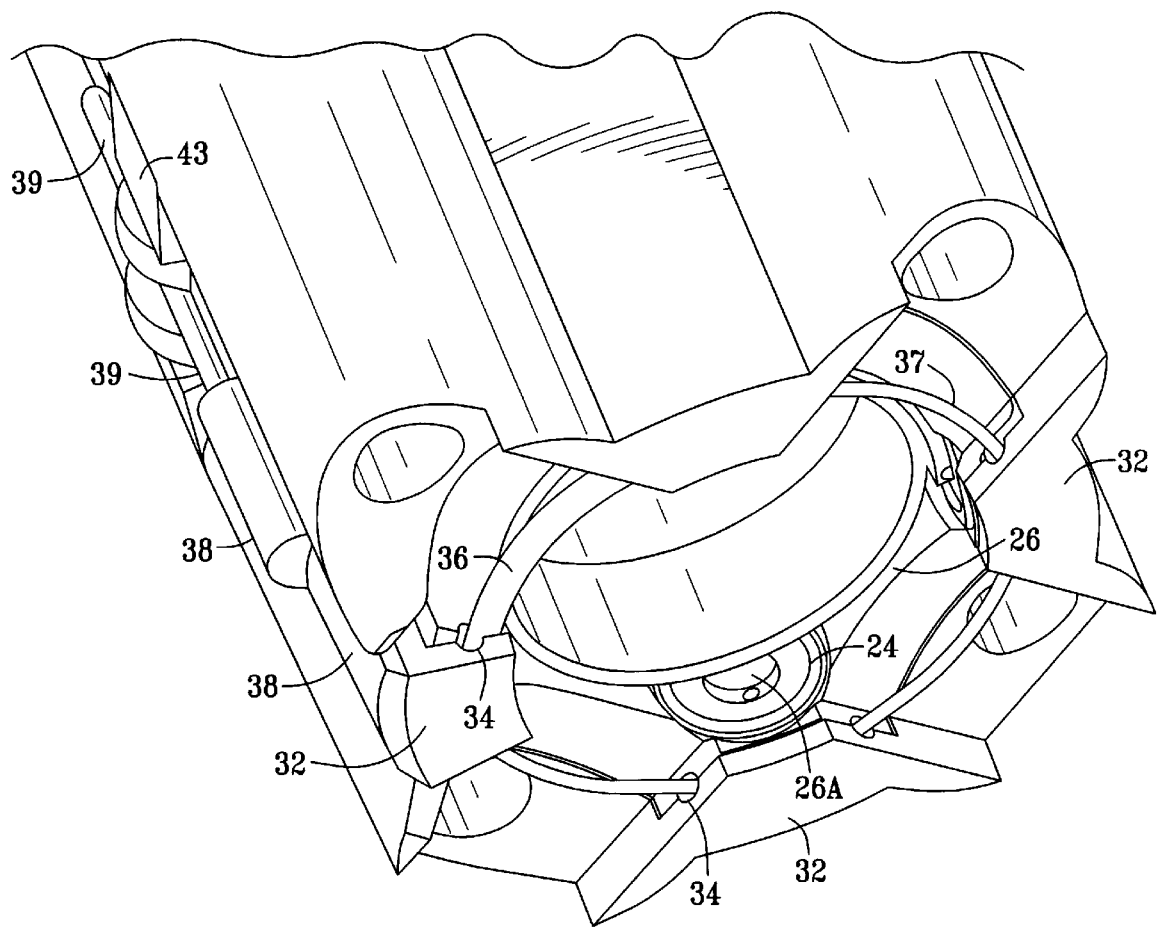
FIG. 6 is a perspective view of an enlarged illustration of the distal end of the tubular structure shown in FIG. 5 having a surgical needle with an attached suture thread operatively positioned within its needle passage and showing one embodiment of a needle removal mechanism in a closed position.

Within the distal end of outer tubular member 12 is a needle advancing mechanism which, in part, consists of a plurality of needle advancing disks or wheels 24 integrally mounted to the inside of outer tubular member 12. Alternatively, as shown in the embodiment of FIGS. 5 and 6, disks 24 are rotationally mounted on a corresponding hub 26a within an annular rack or ring 26. Disks 24 are preferably made of a deformable or compressible material, such as rubber, for facilitating frictional engagement of a needle. The diameter of disks 24 will depend on the size of the purse string suture applicator and the number of disks employed (i.e., more disks, the smaller their diameters), and is about ¼ the diameter of the annular needle passage. Each disk 24 is held in place by means of a clip or pin 27 through hubs 26a. Rack 26 sits on ledges or lips 32 inwardly extending from respective protrusions or peak sections 20. The upper surface 32a of each ledge 32 has an arcuate groove or channel 34 therein which collectively define an annular passage extending 360° for holding an annular surgical needle 36 having suture thread 37 attached thereto. Rack 26 is positioned such that each disk 24 rests upon a ledge 32. More particularly, the circumferential surface of each disk 24 is tangentially aligned with the annular needle passage such that, when an annular surgical needle 36 is operatively positioned within the annular passage, disks 24 frictionally engage needle 36. Accordingly, the rotation of disks 24 cause needle 36 to be advanced through the annular passage. Preferably, then, there is a one-for-one correspondence of disks 24 to protrusions or peak sections 20. Although the embodiment illustrated has four disks 24 and corresponding protrusions 20 (not all are shown), any number of disk-protrusion pairs may be employed by the present invention as dictated by the particular surgical application.

Needle 36 has a sharp point at one end and a suturing thread 37 attached to the other end. It is preferably made of stainless steel, however, other surgical grade materials are suitable. Needle 36 preferably has the same radius of curvature as the annular needle passage 34. The minimum and maximum arc lengths of needle 36 are dependent upon the number of protrusions 20 and, thus, the number of disks 24 employed within the purse string suture applicator of the present invention. Generally, needle 36 has a minimum arc length such that it is in contact with at least one disk 24 at any position when operatively engaged within the annular needle passage. Generally, the maximum arc length of needle 36 is such that it can be easily removed from the annular needle passage. In one embodiment, the maximum arc length of needle 36 is such that it can be radially disengaged from the annular passage by means of a needle removal means, discussed in detail below with respect to FIGS. 6 and 7.

When inner tubular member 14 is operatively positioned inside outer tubular member 12, the distal edge 28 of lower inner tubular section 14b frictionally engages and sits on top of the plurality of disks 24 such that rotational movement of lower section 14b about its longitudinal axis causes each disk 24 to rotate about its respective hub 26a and about an axis which is substantially perpendicular to the axis of rotation of lower section 14b. Needle 36 is caused to rotate in a direction opposite to the direction in which inner tubular section 14 is rotated. A removable handle or knob 30 mounted to the proximal end 29 of top tubular section 14a is provided to facilitate the manual rotation of top section 14a which, by means of the coupling to lower section 14b, in turn rotates lower section 14b. Retainer mechanism 16 limits the downward force imparted by a surgeon or other user to top section 14a from transferring to lower section 14b. As such, the rotational force on disks 24 is optimally fixed (at about 0.5 to 2.5 lbs/sq$^2$) so that disks 24 are able to be rotated in a controlled manner and advance needle 36 freely through the annular passage.

With the present invention, needle 36 may be advanced in a continuous manner through one or more (360°) rotations, or may be incrementally advanced as desired. In most surgical applications, however, it is preferable to provide only a single series or rotation of stitches between trailing thread ends of a purse string suture.

Figure 7:
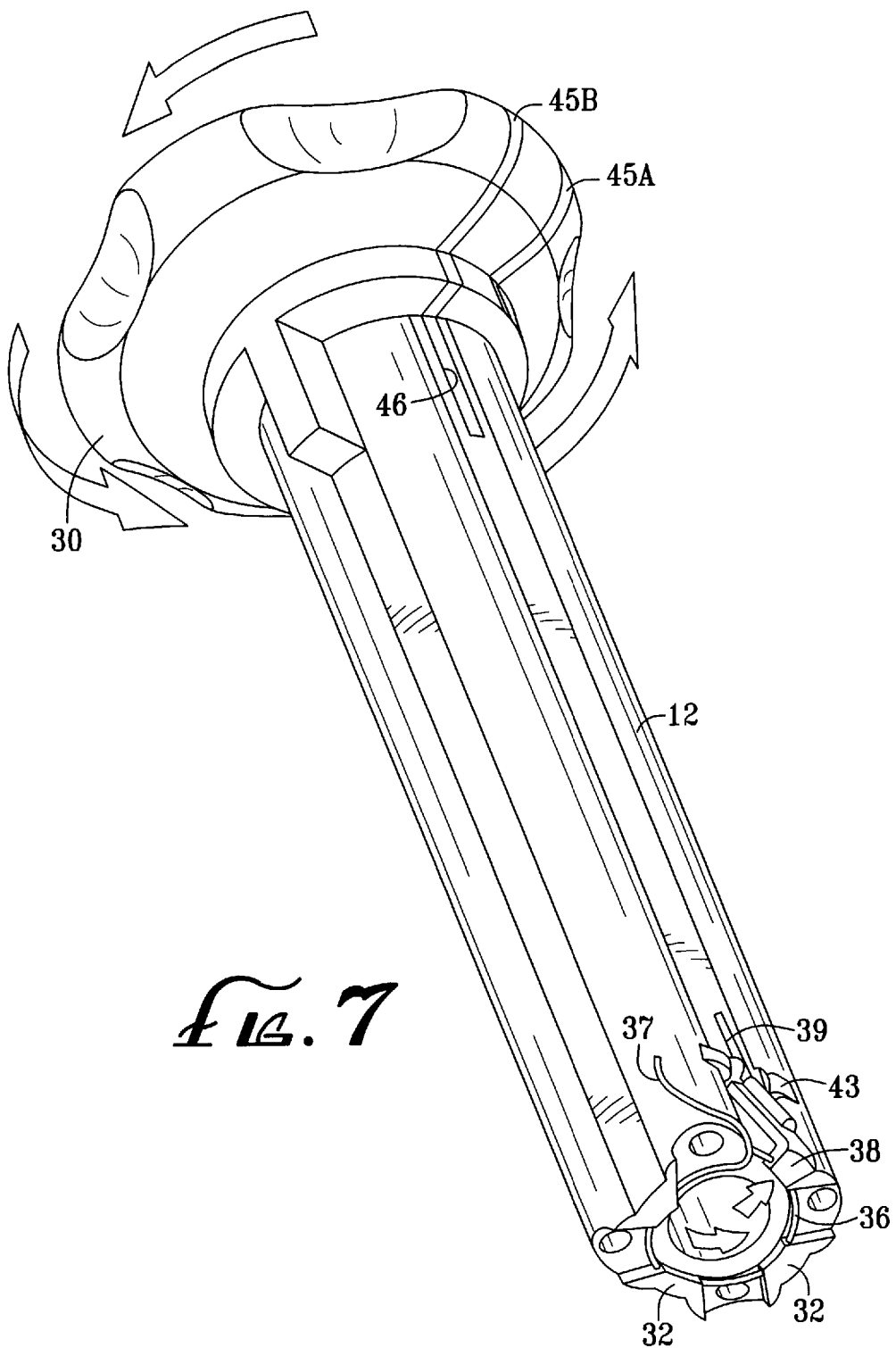
FIG. 7 shows a perspective view of the tubular structure and an attached needle driving knob, both having corresponding markings for proper alignment to ensure timely activation of the needle removal mechanism.

In one embodiment, the purse string suture applicator of the present invention is equipped with a needle removal mechanism which is designed to remove or eject needle 36 from the annular needle passage upon one complete rotation of the needle. As shown in FIGS. 5–7, the needle removal mechanism includes at least one extending section 38 which can be radially disengaged or projected outward from outer tubular member 12. In the embodiment illustrated, extending section 38 is hinged at the outer wall of outer tubular member 12 by means of a wire spring mechanism 39 which is held in place by a pivot clip 43. Spring mechanism causes section 38 to be inwardly biased and in a normally closed position. The needle removal mechanism further includes an annular recess or groove 40 circumferentially disposed about the distal end 41 of tubular lower section 14b, and a ramped notch 42 protruding from the inner wall of radially disengageable section 38 and which is received within annular recess 40. Annular recess 40 encircles slightly less than 360° of distal end 41 and thereby defines a contact point 44 whereby the radially disengageable section 38 is projected radially outward from outer tubular section 12 when contact point 44 is caused to engage notch 42. Preferably, section 38 is caused to disengage with needle 36 disposed within its respective arcuate channel 34 after needle 36 has substantially traveled one rotation through the annual needle passage.

In order to ensure that needle 36 is not prematurely disengaged, i.e., prior to completing all of the stitches (the number of stitches or "bites" of tissue being defined by the number tissue bays 22) of the purse string suture, hatch marks 45a and 45b are preferably provided on outer tubular housing 12 for rotational alignment with corresponding hatch mark 46 on inner tubular housing 14 and/or knob 30. Alignment of hatch mark 45a with hatch mark 46, properly positions inner tubular housing 14 prior to rotation of knob 30 and, in particular, positions annular recess 40 about ramped notch 42 such that notch 42 is allowed to travel the entire arc length of recess 40 before notch 42 engages contact point 44. Alignment of hatch mark 45b with hatch mark 46 indicates that needle 36 has been removed or disengaged from the annular needle passage by the radially disengagement of section 38 as shown in FIG. 7. The hatch marks are particularly helpful when operating the purse string suture applicator through minimally invasive surgical openings which provide limited visual access. Such a marking protocol further ensures that purse string suture applicator is not removed from a target site while a needle is embedded within the tissue.

Figure 8A:
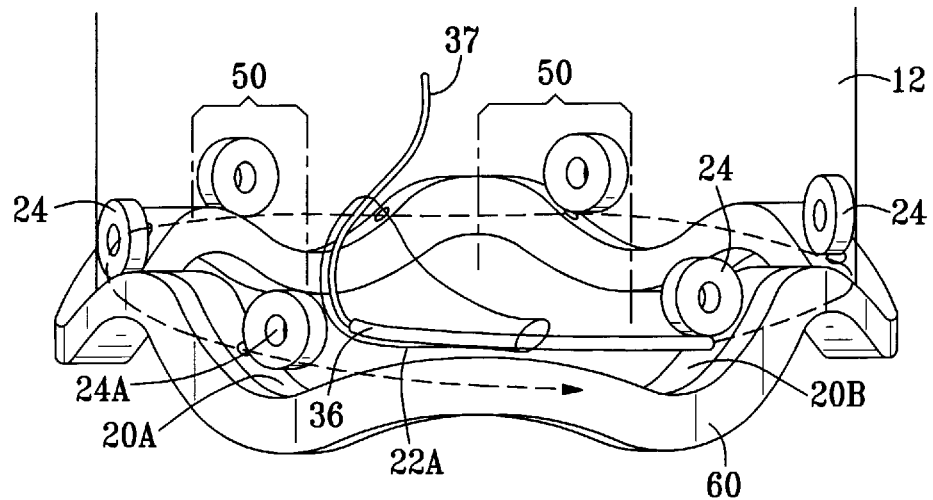
FIGS. 8A and 8B illustrates the tubular structure having an alternate embodiment of a means for removing a needle from the needle passage.
Figure 8B:
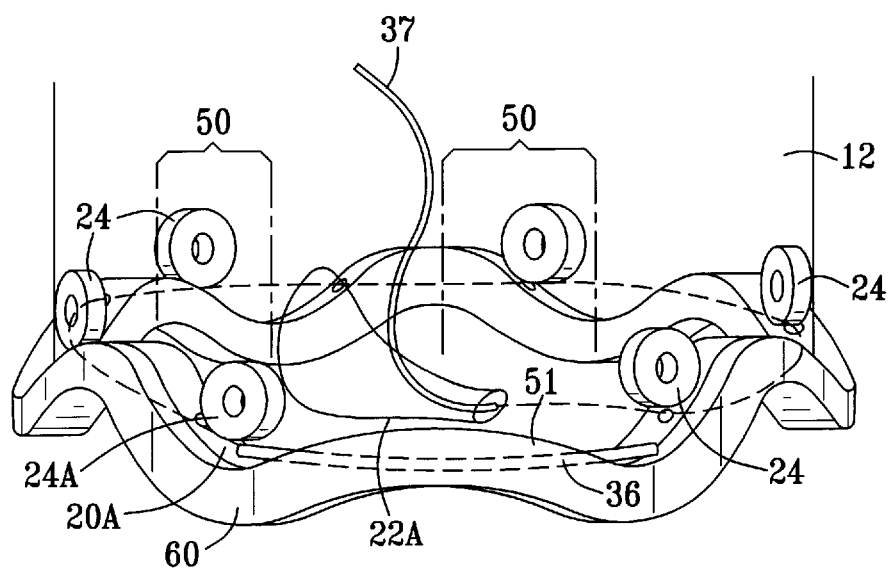

In an alternate embodiment, as shown in FIGS. 8A and 8B, the annular needle passage (identified in phantom) defined within the distal end of outer tubular member 12 is slightly helical or spiraled such that a needle 36 operatively positioned therein advances in a slightly downward helix. In other words, needle 36 commences its advancement through the passage at a level or position (see the cut-away portion in outer tubular member 12 as illustrated in FIG. 8A) which is more elevated than or proximal to the position or level (see the cut-away portion in outer tubular member 12 as illustrated in FIG. 8B) at which needle 36 is in upon completion of one revolution through the annular passage. To effect this helical passage, the distal end of outer tubular member 12 has two consecutive extending sections 20a and 20b and the common tissue bay 22a therebetween which, collectively, are less contoured than the remainder of the distal end. Additionally, the plurality of disks 24, which, in the embodiment of FIGS. 8A and B, number six to correspond with the six extending sections 20 of outer tubular member 12, and unlike the above embodiments, are not centrally aligned with the extending sections 20 but are proximately positioned to respective sloping portions 50 between extending sections 20 and tissue bays 22. As such, the disk 24a, which is the last disk engaged by needle 36 before completing a revolution and which is approximately aligned with section 20a, is slightly, vertically offset or lower than the other disks 24. Needle 36 is caused to exit its helical path and engage from the tubular structure at a defined exit point 51. Thus, upon a complete revolution within the annular passage, needle 36 is advanced through the wall of the vessel lumen 60 and then directed downward and out of outer tubular member 12. The needle can then be grasped and the tubular structure 10 is freely removed, unencumbered by the attached suture thread 37 and trailing end thereof.

With all embodiments of the present invention, irrespective of the needle removal means employed, needle 36 is preferably preloaded in a selected position within the annular needle passage to further ensure the complete and proper placement of all stitches, and ensure timely disengagement, if necessary, of a needle from the tubular structure.

As mentioned above, the maximum arc length of needle 36 is such that it can be removed, driven out, or radially disengaged from the annular passage by means of a needle removal mechanism or means such as those described above. For example, in the embodiment employing a radially disengageable section 38, the arc length of the needle used is preferably not greater than the width of section 38 so as to be free from catching onto or tearing through tissue held within the tissue bays 22 on either side of section 38 when being removed from an operative position within the annular passage. Similar limitations are true for suture applicators employing other needle removal means. Furthermore, for any embodiment, the arc length is further dictated by the number of extending sections 20 and disks 24 that are employed. The more sections 20 and disks 24, the less clearance there is for removal of a needle from a tissue bay 22, and thus, the shorter the needle must be. For example, a purse string suture applicator having four disks 24 and extending sections 20 should employ a needle having a minimum arc length of no less than about ¼ the are length of the annular needle passage. Similarly, an applicator having six disks 24 and corresponding sections 20 should employ a needle having a maximum arc length of no more than about ⅙ that of the annular needle passage.

Based on the particular contours, configuration, or pattern (e.g., sinusoidal, castellated, etc.) of distal edge 19 of outer tubular member 12, the exact shape or form of the compressed tissue 60 will vary, but preferably takes on a substantially sinusoidal configuration for any configuration of distal edge 19 as shown in FIG. 9. Specifically, a schematic representation is provided of a silhouette of an outer tubular member 12 operatively engaging the wall of a cut-away of a vessel lumen 60. The distal edge 19 of outer tubular member 12 has a substantially sinusoidal configuration having, for example, six protrusions 20 and corresponding tissue bay sections 22 such that the tissue conformed thereto takes on a similar, substantially sinusoidal configuration having six peaks 61 and valleys 62. A needle 36 with an attached suture thread 37 is shown having been advanced through the portion of tissue wall engaged within tissue bays 22. The resulting purse string suture is shown in FIG. 10 where thread 37 has been passed four times through the wall of vessel lumen 60 (only a cut-away portion is shown) with two trailing ends 37a and 37b remaining after the needle 36 has been cut off.

Another aspect of the present invention is that, if desired, a purse string suture may be provided which penetrates through less than the entire thickness of the tissue wall when it is necessary to avoid complete penetration of the wall, such as in the aorta. This application is illustrated in FIGS.

11A and 11B. FIG. 11A schematically shows two needle advancing disks 24 driving a needle through respective arcuate channels 34 of sections 20, and penetrating tissue wall 60 which has been conformed to the sinusoidal distal edge of outer tubular member 12. The vertical distance 53 from the distal edge at the midpoint of an extended section 20 to the distal side of needle 36 is selected such that needle 36 does not penetrate through the entire thickness 55 of tissue wall when advanced therethrough. Preferably, the value of distance 53 is one third (⅓) to two thirds (⅔) less than tissue wall thickness so as not to completely penetrate the wall thickness 55 and to minimize the risk that the applied suture will tear through the tissue wall when pulled or tightened. The thickness of the tissue wall ranges from 1 to 3 mm for the aorta, 1 to 2 mm for the vena cavae, and 1–3 mm for the atrium. Accordingly, distance 53 will range from less than 1 mm to about 2 mm depending on the vessel being sutured. The vertical distance 54 from the distal edge at the midpoint of an extended section 20 to the midpoint of a tissue bay 22 is preferably between about 1.5 to 3.5 mm.

In addition to the above described tubular structure 10 and the various components integral to it, the purse string suture applicator of the present invention further includes means for releaseably engaging or compressing the tissue to be sutured into the several tissue bays or valleys 22 of the outer tubular member 12. FIGS. 12–16 illustrate various embodiments of such a tissue engaging or compressing means and methods of engaging or compressing tissue against the distal edge of tubular structure 10. For each of the embodiments shown, a schematic illustration is provided of the distal section of tubular structure 10 having outer 12 and inner tubular members 14 operatively engaged against the outer wall of a segment of vessel lumen 60. As discussed above, outer tubular member has an optimally contoured distal edge for engaging and conforming the tissue wall, and inner tubular member 14 generally functions to drive or advance an arcuate needle (not shown) through an annular passage internal to and within the distal end of tubular structure 10. Additionally, for each embodiment illustrated, a proximal portion of either tubular structure 10 or an actuator mechanism for the tissue engaging means is shown.

Figure 12:
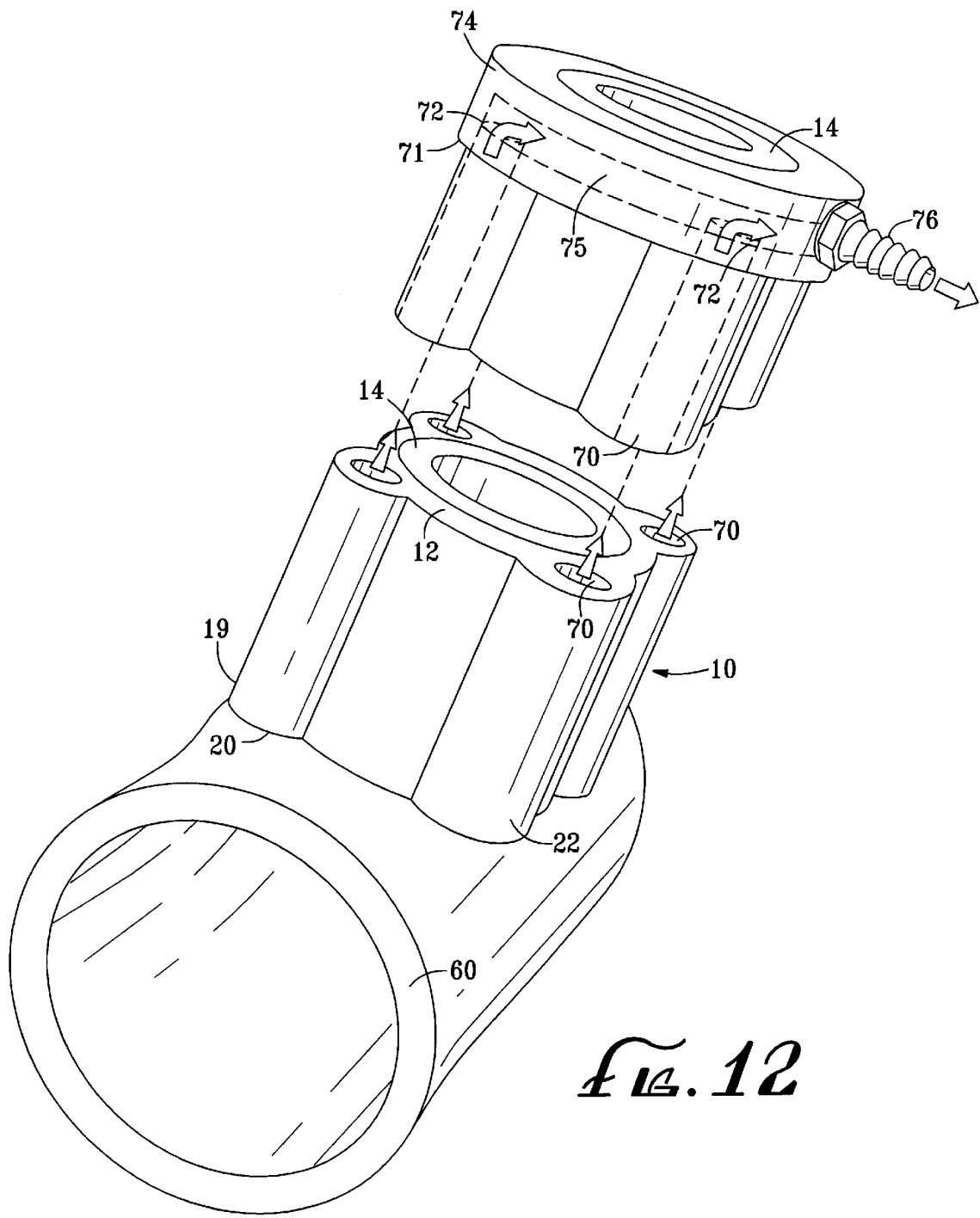
FIG. 12 is a schematic illustration of a purse string suture applicator of the present invention having a suction-based means for engaging the tissue against the distal end the tubular structure.

In the schematic drawing of FIG. 12, a preferred embodiment is shown employing suction or negative pressure to draw up or engage tissue into tissue bays 22. Integral to tubular structure 10,and housed within outer tubular member 12 are a plurality of pneumatic pathways 70, and preferably there is a one-for-one correspondence of pathways to tissue bays 22. A pathway 70 extends from a distal port (not shown) flush with the distal edge 19 at each tissue bay 22 to a proximal port 72 at the proximal edge 71 of outer tubular member 12. The means for applying a negative pressure through pneumatic pathways 70 includes an annular attachment head 74 configured to sealingly engage with the proximal edge 71 of outer tubular member 12. An annular channel 75 is housed within annular attachment head 74 and is pneumatically connected with each pneumatic pathway 70. A port 76 pneumatically connects channel 75 to a vacuum or negative pressure source (not shown), which may be any model suitable for use in surgical applications. Upon application of negative pressure to port 76, the wall of the vessel lumen 60 is drawn against the distal edge between the protrusions 20, conforming the wall to a substantially sinusoidal configuration. The needle (not shown) can then be advanced through the internal annular channel (not shown) and the tissue segments held within tissue bays 22 by rotating inner tubular member 14 as discussed above with respect to FIGS. 1–7. Once the needle has completed a revolution, the vacuum source can be turned off to release the tissue from the tissue bays 22.

Figure 13:
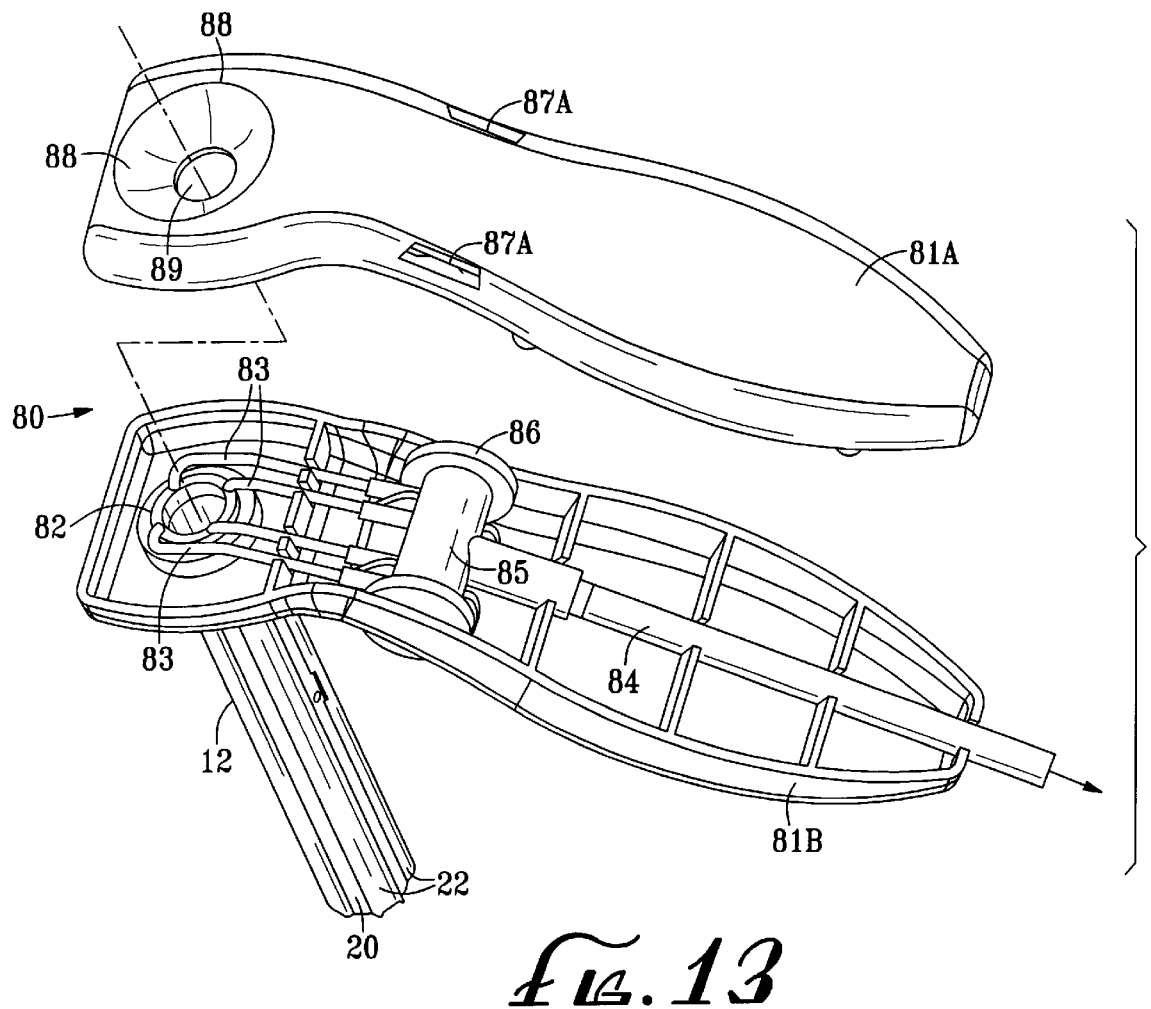
FIG. 13 is an exploded view of a purse string suture applicator employing an alternate suction-based means for engaging tissue.

FIG. 13 shows an alternate embodiment of a suction-based means for engaging tissue against distal edge 19. A suction device 80 is provided wherein the top portion 81a of a preferably plastic-molded, handle-shaped housing 81 is shown exploded away from the bottom portion 81b of the housing to display the internal structure of the device 80. Device 80 has an annular attachment head 82 which is configured to easily and quickly "snap onto" and become sealingly engaged to the proximal end of outer tubular member 12, such as that shown in FIG. 12, wherein proximal ports 72 are automatically aligned and in pneumatic connection with corresponding vacuum tubes 83. Vacuum tubes 83, which are made of stainless steel or can be flexible plastic tubing, extend rearwardly within housing 81 where they are collectively coupled to a single pneumatic connection tube 84 which in turn extends out of housing 81 to a vacuum source (not shown). A spool-shaped vacuum actuator or switch 85 is provided on top of and is rotationally engageable with vacuum tubes 83 to control the application of negative pressure through vacuum tubes 83. Actuator 85 includes dual dials 86 sized to extend through openings 87 in upper housing 81a and corresponding openings (not shown) in lower housing 81b when the two housing sections are sealed together, forming a handle. Handle 81 is intended to be ergonomically held within one hand, and dials 86 are positioned to be rotationally adjustable by the thumb of the hand in which the device 80 is held. Vacuum tubes 83 are in a normally open state, providing suction through pneumatic pathways 70 and causing tissue to be engaged within tissue bays 22 (see FIG. 12). When rotated forward towards annular attachment head 82, actuator 85 is caused to compress vacuum tubes 83, closing off the negative pressure to pneumatic pathways 70 and releasing tissue from tissue bays 22. The forward end of housing 81 comprises a funnel-shaped portion 88 having an opening 89 extending through annular attachment head 82. A needle driving actuator, such as knob 30 in FIGS. 1–4 and 7, may be positioned within opening 89 and operatively coupled to the proximal end 29 (see FIG. 3) of inner tubular member 14 for driving a needle during the application of suction.

Turning to FIG. 14, another embodiment of the present invention is provided which employs a plurality of grasping members 90 integrally adapted to outer tubular member 12 for grasping tissue 60. Each grasping member 90 includes a pair of coacting jaws 97 which define a tissue bay 22 and are operatively configured to grasp tissue. Coacting jaws 97 preferably have teeth at their distal ends to facilitate the a traumatic grasping of tissue. Coacting jaws 97 articulate about a hub 98 having a ribs 98a which ride in an opposing groove 97a on the inside surface of each coacting jaw 97. For purposes of illustration, grasping member 90a (left-hand side as viewed) is shown to be in a normally open position. Conversely, for purposes of illustration, grasping member 90b (right-hand side as viewed) is shown in a closed or grasping position; however, it should be noted that all grasping members 90 work synchronously such that all are simultaneously open or closed. Jaws 97 are mounted to plate 93 by means of retainer posts 93a. For each grasping member 90, a rod 91, which is slideably engaged within and extends longitudinally through a respective lumen of the wall of outer tubular member 12, extends distally through a bore in retainer plate 93b and is fixed to hub 98. At its proximal end, rod 91 is coupled to an actuator mechanism 92 which acts to pull up on rod 91 to close jaws 97 (as seen by grasping member 90b).

Actuator mechanism 92 comprises two stacked annular sections, a lower section 100 which is rotatably mounted to the proximal end of outer tubular member 12, and an upper section 101, which is moveable only in a vertical direction along the axis of the tubular structure. Each of sections 100 and 101 have multiple cam protrusions on their opposing surfaces. Each protrusion has a vertical side 100a, 101a and a ramped side 100b, 101b to produce a rectilinear motion upon rotating lower section 100. The proximal end of each rod 91 extends through and is movable within an arcuate slot 102 within lower section 100, and is rigidly fixed to upper section 101. The left-hand portion of actuator mechanism 92 shows sections 100 and 101 "seated" within each other, maintaining respective rod 91a in a lower position, and thus, jaws 97 of grasping member 90a in an open position. Rotating lower section 100 in the clockwise direction from this seated position causes sections 100 and 101 to become unseated, as shown in the right-hand portion of actuator mechanism 92, pulling up on respective rod 91b. A spring coil 94 that encircles rod 91 and is positioned between plate 93b and the "arch" 104 of outer tubular member 12, acts to bias grasping member 90b vertically downward. In the course of rotation of lower section 100 of actuator mechanism 92, when ramped sections 100b and 101b are engaging each other, the spring bias causes plate 93b to push down on and close coacting jaws 97 around the area of tissue upon which they are positioned. As the rotation continues and sections 100 and 101 become fully unseated from each other, the bias of spring 94 is overcome, causing grasping member 90b to be pulled into tissue bay 22.

It is intended that the needle driving action of the present invention occur upon recession of the tissue into tissue bays 22. To this end, a needle driving actuator, such as knob 30 in FIGS. 1–4 and 7, may be positioned within tubular structure 10 to engage with inner tubular member 14 (see FIG. 3) for driving a needle during actuation of grasper members 90.

With respect to the embodiments of FIGS. 12–14, after the application of the purse string suture is complete, and the purse string suture applicator has been removed from the surgical area, it is necessary to create an incision in the vessel lumen 60 for insertion of a cannula. This is commonly done by means of an independent surgical instrument, typically a scalpel or trocar. However, it is contemplated, as shown in FIG. 18, that an integral cutting element, such as blade 150, be housed within tubular structure 10. As shown, blade 150 is hinged to the distal end of a rod 158 which extends through inner tubular member 14. Blade 150 is preferably made of stainless steel and has a length that extends between the inner and outer diameters of inner tubular member 14. The hinged end 152 of blade 150 has a notch 153 which firmly engages a recessed spring plate 155 embedded in the wall of inner tubular member 14. Hinged end 152 resides within a first slotted recess 156 in inner tubular member 14, causing the length of blade 150 to be normally positioned substantially perpendicular to the longitudinal axis of tubular structure 10. The opposite end of blade 150 extends into a second slotted recess 157 within inner tubular member 14, directly opposite of first slotted recess 156. Recess 156 and 157 are each located between adjacent disks 24 so that motion of blade 150 is not impeded by disks 24. Further, blade 150 is positioned such that the plane in which it moves bisects the cross-sectional area of the lumen defined by inner tubular member 14. After a purse string suture (not shown) has been provided, a cannula 160 can be inserted into inner tubular member 14 to engage blade 150, causing it to overcome the bias of spring plate 155 and rotating it radially about hinged end 152. After cutting into the wall of vessel lumen 60, blade 150 comes to rest at a position parallel to the longitudinal axis of tubular structure 10. Rod 158 extends proximally through the proximal end of inner tubular member 14 and is controllable by a surgeon to axially rotate blade 150 90° so that blade 150 is substantially flush with the inner wall of inner tubular member 14. When flush, cutting edge 162 of blade 150 is not exposed and cannot cut the sutures that have been placed. After the tip of cannula 160 has been properly inserted, tubular structure 10 is removed and the purse string suture can be firmly cinched around cannula 160.

Other embodiments of the tissue conforming means of the present invention are illustrated in FIGS. 15–17. Common to each of these other embodiments is a deployable or expandable mechanism which is inserted into the tissue structure or lumen and deployed or expanded to compress the tissue wall against the contoured distal edge of tubular structure 10. The particular deployable or expandable mechanism may comprise a balloon (FIG. 15), an expandable braided material (FIG. 16), an umbrella-like device (FIG. 17), or combinations of thereof which are operable between open (expanded or deployed) and closed (constricted or deflated) positions. An expansion or deployment actuator mechanism is proximally provided to be easily controlled by a surgeon. A rigid elongated tube operatively extends between the actuator mechanism and the deployable/expandable member which, in a closed position, may be configured so as to form a pointed cutting or puncturing tip to penetrate the tissue around which the purse string suture is to be placed and through which the deployable/expandable mechanism is delivered. This puncture site readily provides an opening for the entry of a cannula within the vessel lumen 60. Thus, these embodiments eliminate the need to use a separate surgical instrument, such as a scalpel or trocar, to create a cannula entry site.

Figure 15B:
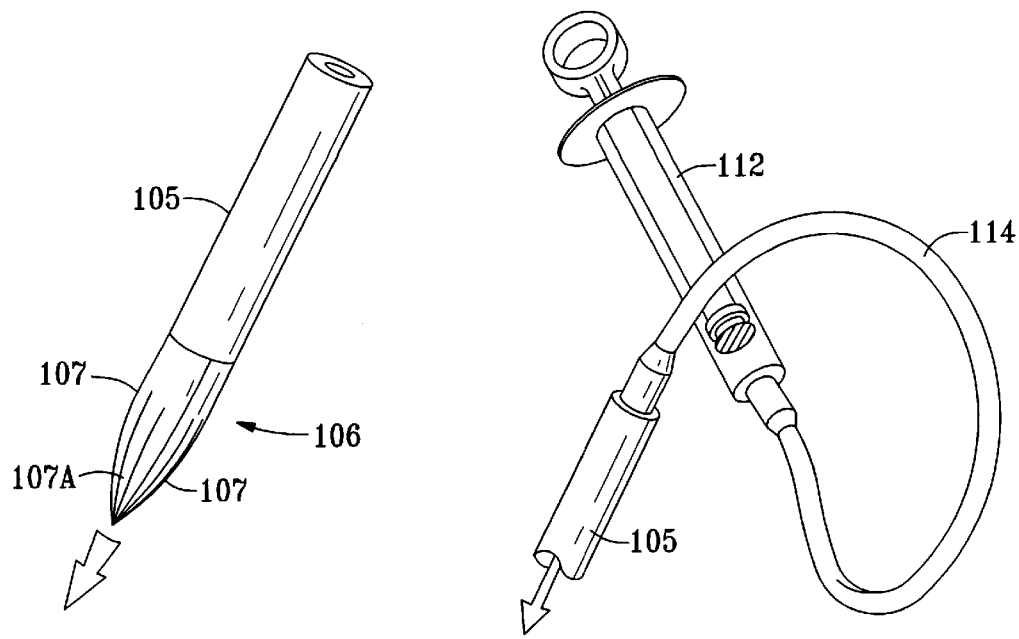
FIG. 15B shows the distal end of the tissue compressing device of FIG. 15A when in a closed position. The tip of the distal end is configured to have a trocar-like pointed tip for puncturing tissue.
Figure 15A:
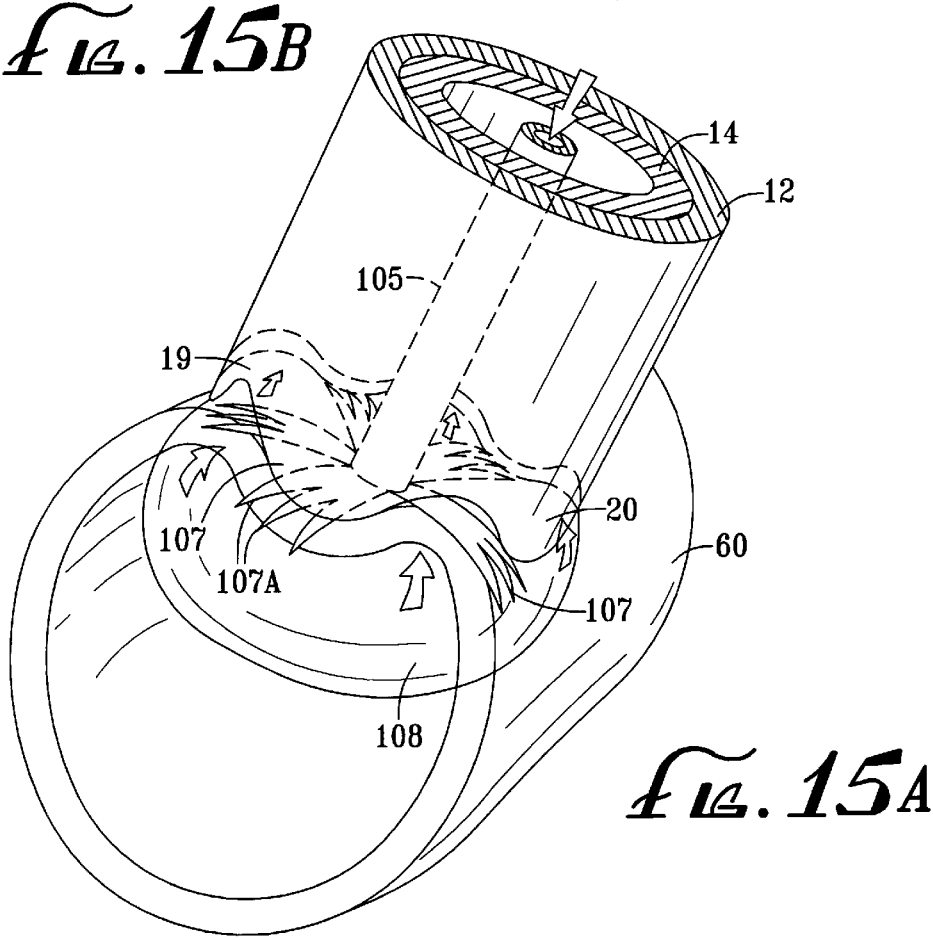
FIG. 15A is schematic representation of another embodiment which employs an expandable balloon mechanism in an expanded or inflated condition for compressing the wall of the vessel lumen to be sutured against the distal edge of the tubular structure.

FIG. 15 shows a balloon-type mechanism for conforming tissue which has been inserted axially through outer 12 and inner 14 tubular members. The mechanism includes a rigid slender introducer tube 105 which is preferably made of a polymeric material. The distal tip 106 of introducer 105 consists of a plurality of deployable structural support members 107 which, when in a closed position as shown in FIG. 15A, form a trocar-like point which is capable of puncturing tissue. In the closed position, tip 106 retains an expandable balloon 108 which is in fluid communication with an inflation/deflation mechanism 112 via a flexible, catheter-like tubing 114. Alternatively, the inflation/deflation mechanism 112 is preferably a syringe for delivering a fluid, such as saline, to expand or inflate balloon 108 as well as to deflate balloon 108. Balloon 108 has an expanded volume which can be a traumatically accommodated by the vessel or lumen in which it is inserted. Balloon 108 is preferably made of latex or another suitable elastomeric material and is preformed in a configuration which readily conforms to the configuration of the distal edge 19 of outer tubular member 12. Preferably, then, the top surface of balloon 108 is preformed in a substantially sinusoidal shape to match the preferably substantially sinusoidal configuration of distal edge 19. Structural support members 107 have fingers 107a which, when in an open or deployed position as shown in FIG. 15, spread apart from each other. Structural support members 107 are preferably made of flexible stainless steel so as to be rigid enough to penetrate tissue when closed but flexible enough to accommodate expansion of balloon 108. Although not necessary for conforming balloon 108 to distal edge 19, support members 107 help to further maintain balloon 108 in its preformed configuration, and are intended to be aligned under protrusions 20 of outer tubular member 12 when operatively positioned within the targeted tissue structure 60. Alternately, a very thin, flexible metallic ring (not shown) may also be provided on the preformed surface of balloon 108. The ring would follow the sinusoidal path to guard against the possibility of a needle puncturing balloon 108 in the case where the tissue wall 60 is exceptionally thin.

Upon expansion of balloon 108, a needle driving actuator, such as knob 30 in FIGS. 1–4 and 7 but having an annular configuration so as to accommodate the actuator mechanism 112, catheter 114 and tube 105, can be used to rotationally advance a needle through the tissue within tissue bays 22. As mentioned above, the annular needle passage is configured such that a needle is driven through less than the entire thickness of the tissue wall, obviating the risk of the needle puncturing balloon 108. To remove balloon 108 from vessel lumen 60, the expansion fluid is withdrawn by means of syringe 112, and tube 105 is pulled up through tubular structure 10.

FIGS. 16 and 16A show another embodiment of the tissue compressing means of the present invention employing an umbrella-like deployment mechanism 110 having a plurality of support members 111. Support members 111 have substantially rectangular shapes with tapered ends to provide a stream-line shape for puncturing tissue 60 but may, however, be cylindrical or have any other suitable shape. Support members 111 are attached to introducer tube 105 by individual hinge mechanisms 119 which allow outward deployment of members 111. Their lengths are approximately that of the radius of outer tubular member 12, thus, allowing them to be deployed at right angles to tube 105 within vessel lumen 60 without contacting the inner tissue wall opposite the puncture site.

Similar to the embodiment of FIGS. 15A and 15B, a rigid elongated introducer tube 105 extends between deployment mechanism 110 and an actuator mechanism or rotatable knob 115. Extending through tube 105 is a rod 116 which terminates distally in a somewhat bulbous member 121 having pointed tip 117 which is suitable for puncturing vessel lumen 60 to provide an entry site for deployment mechanism 110. Rod 116 is threaded at its proximal end to a threaded receptacle (not shown) within knob 115, such that when knob 115 is rotated in a counter-clockwise direction, rod 115 is caused to travel upward.

When axially introduced through tubular structure 10, tip 117 punctures vessel lumen 60 introducing deployment mechanism 110 within vessel lumen 60. Actuation of rod 116 causes member 121 to move upwards and engage the inner surfaces of support members 111, forcing them to deploy radially outwards. The final position of support members 111 is locked by the geometry of tip 117. When operatively positioned, there is a one-for-one alignment of support members 111 within tissue bays 22, causing tissue there between to conform to the distal edge of outer tubular member 12. A needle driving actuator, such as knob 30 in FIGS. 1–4 and 7 but having an annular configuration so as to coaxially accommodate the actuator mechanism 115 and tube 105, can be used to rotationally advance a needle through the tissue within tissue bays 22. After a complete rotation of the needle through the tissue, the support members 111 are retracted radially inwards by means of rotating knob 115 clockwise, and tube 105 is pulled up through and out of tubular structure 10.

Another embodiment of the tissue conforming means is illustrated in FIGS. 17A and 17B. Here, the deployment mechanism 130 consists of an expandable cylindrical sheath 131, such as a polymeric braid (e.g., polyethylene). Also included are an elongated rigid introducer tube 105, a rod 116, pointed tip 117, and an actuator mechanism (not shown), such as the rotatable knob 115 described with respect to FIG. 16A, which are structurally and functionally similarly to the embodiment of FIGS. 16A and 16B. The distal end of sheath 131 is attached to pointed tip 117 and the proximal end is attached to the distal end of tube 105. In a closed position, as shown in FIG. 17B, braided sheath 131 is compressed and maintains a profile which facilitates the entry into vessel lumen 60. Optionally, a plurality of spaced-apart, flexible braces or support members 132 are provided which are attached to and extend along the length of braided sheath 131, creating spaced-apart braided segments 133.

When the actuator mechanism 115 is rotated in a counter-clockwise direction, rod 116 and tip 117 travel upward, causing braided sheath 131 to fold or buckle and expand radially outward as tip 117 moves closer to the distal end of tube 105. The length of sheath 131 and braces 132 are such that the entire length of deployment mechanism 130 can be inserted into lumen 60 without tip 117 contacting the inner tissue wall opposite the puncture site. Similarly, the length is such that the distance which sheath 131 is caused to radially expand is not substantially greater than the radius of outer tubular member 12.

When operatively positioned, there is a preferably a one-for-one alignment of braces 132 within tissue bays 22, causing tissue there between to conform to the distal edge of outer tubular member 12. A needle driving actuator, such as knob 30 in FIGS. 1–4 and 7 but having an annular configuration so as to coaxially accommodate the actuator mechanism 115 and tube 105, can be used to rotationally advance a needle through the tissue within tissue bays 22. After a complete rotation of the needle through the tissue, tip 117 is caused to travel downward, stretching sheath 131 and braces 132 into their closed positions, and tube 105 is pulled up through and out of tubular structure 10.

Figure 19:
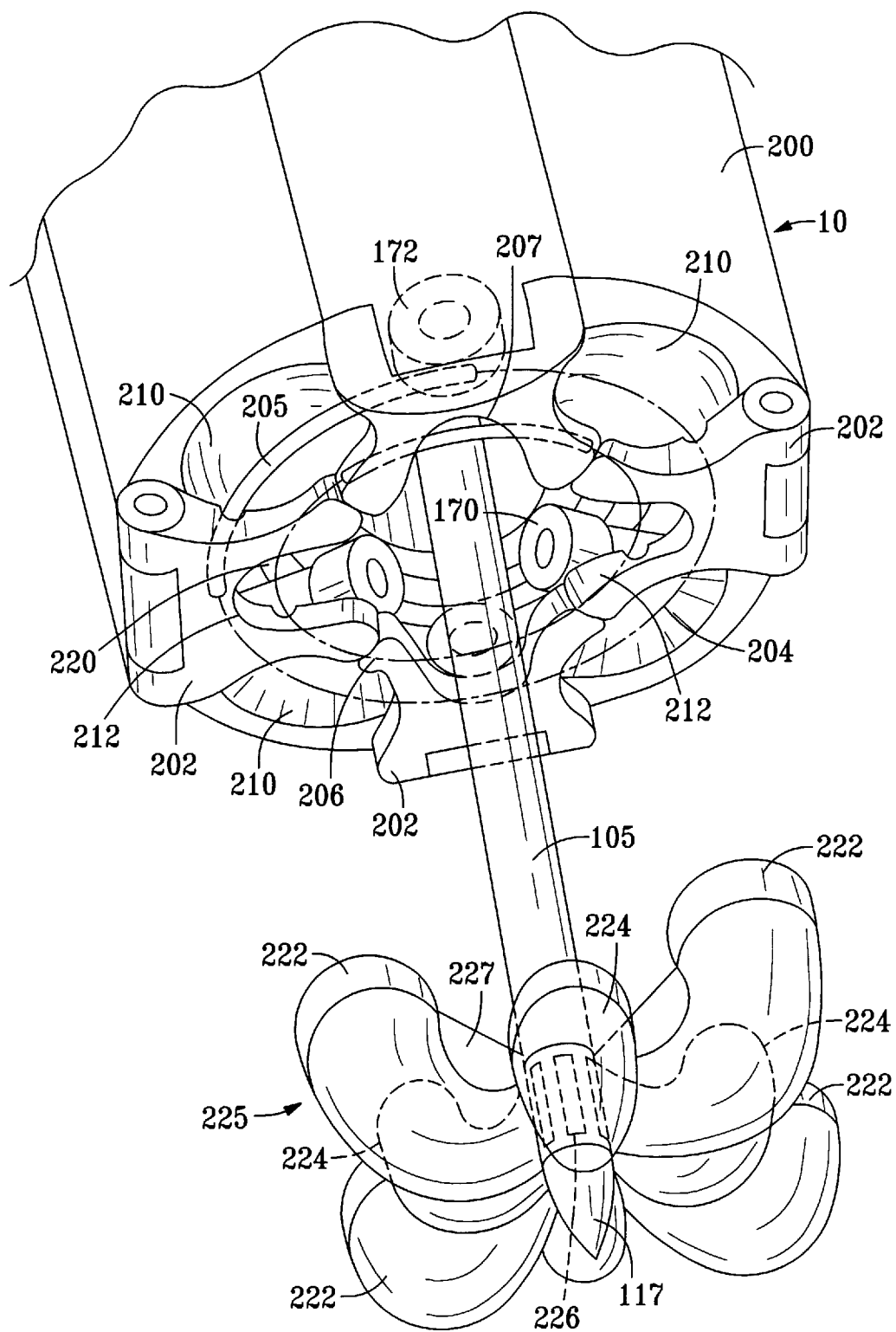
FIG. 19 is an embodiment of a dual purse string suture applier for placing two concentric rows of purse string sutures in a vessel wall.

Turning now to FIG. 19, there is shown the distal end of an embodiment of a dual purse string suture applicator for simultaneously applying two concentric rows of purse string sutures, as required for aortic cannulation. A tubular structure 10 includes an outer tubular member 200 having a plurality of distally hinged H-shaped segments 202 (four are shown but more may be employed) having two concentric annular needle passages, outer needle passage 204 and inner needle passage 206. As best that can be viewed in FIG. 19, an inner tubular member 220 engages two concentric sets of disks, outer set 172 and inner set 170 which act to rotationally engage annular needles 205 and 207, respectively. Inner tubular member 220 and disks 170 and 172 function in a fashion similar to previously discussed embodiments.

Segments 202 define an outer and inner set of tissue bays 210 and 212, respectively, which are shaped to receive an outer and inner set of fingers 222 and 224, respectively, of tissue conforming means 225. Based on this configuration, needles 205 and 207 are preferably preloaded so as to be offset approximately 45° from each other, as shown in FIG. 19.

As with the embodiment of FIG. 15A, tissue conforming means 225 is comprised of a preformed latex balloon which, in a deflated condition, is housed within the distal end of rigid elongated introducer tube 105. In the deflated condition, tip 117 is used to puncture a vessel lumen (not shown) and deliver the distal end within the lumen. By means of an inflation/deflation syringe similar to that shown in FIG. 15A, fluid is injected into balloon 225 to expand preformed fingers 222, 224 radially outward and upward from slots 226 circumferentially disposed about the distal end of tube 105. Fingers 222, 224 are maintained in an upward position by a respective webbed sections 227. After expansion, fingers 222, 224 are drawn up to compress the wall of the vessel lumen into respective tissue bays 210 and 212. Needles 205 and 207 can then be advanced through the tissue within the tissue bays. After the dual purse string sutures are placed, balloon 225 is deflated and fingers 222, 224 are withdrawn into introducer tube 105. Tubular structure 10 is then slightly lifted to allow hinged segments 202 to be radially disengaged by means of a proximally-controlled rod (not shown) housed within outer tubular member 200. Needles 205 and 207 can then be grasped, and pulled through their last stitch or "bite," if necessary.

Various embodiments of a purse string suture applicator and methods for using the same have thus been described for automatically applying a purse string suture to tissue in vivo through any sternal or thoracic surgical opening including, but not limited to, a sternotomy, thoracotomy, mini-sternotomy, mini-thoracotomy, and transthoracically through a trocar sheath. In particular, application of a purse string suture to one wall of a vessel lumen, often required in cardiac surgery for the purpose of cannulating the heart and major vessels of the heart, has been described. A preferred aspect and method of the present invention is to provide a purse string suture which extends through less then the entire thickness of the tissue wall. Furthermore, those skilled in the art will appreciate that the present invention greatly reduces the time necessary to place a purse string suture.

Although the devices and methods of the present invention have been described in some detail by way of illustration and example, it will be readily apparent to those skilled in the art that certain modifications and other embodiments may be practiced without departing from the spirit and scope of the invention and which are within the scope of the appended claims. For example, although the purse string suture structure and the associated needle passage therein have been preferentially described to have tubular and annular configurations, respectively, it will be understood by those skilled in the art that other configurations which are suitable for providing a purse string suture are acceptable for the present invention.

What is claimed is:

1. An apparatus for automatically applying a purse string suture in the wall of a vessel lumen, comprising:
   an elongated structure having a distal edge comprising a plurality of spaced-apart protrusions;
   a needle passage defined within said distal edge;
   means for advancing an needle through said needle passage; and
   means for releasably engaging the wall of a vessel lumen against said distal edge of said elongated structure.

2. The apparatus of claim 1 wherein said elongated structure is tubular and said needle passage is annular wherein an annular needle is advanceable therethrough.

3. The apparatus of claim 1 wherein said plurality of protrusions form a substantially sinusoidal pattern.

4. The apparatus of claim 1 wherein said plurality of protrusions form a substantially castellated pattern.

5. The apparatus of claim 1 comprising four, five, or six protrusions.

6. The apparatus of claim 1 wherein the distance between the distal side of said needle passage and said distal edge of said structure at the midpoint between adjacent protrusions is less than the thickness of the vessel lumen wall.

7. The apparatus of claim 2 wherein said means for advancing an annular needle through said annular needle passage comprises a plurality of rotatable disks integrally mounted within said tubular structure wherein the circumferential surface of each said disk is tangentially aligned with said needle passage such that rotation of said disks advances an annular needle through said annular passage.

8. The apparatus of claim 2 wherein said means for releasably engaging the wall of a vessel lumen comprises:
   a plurality of pneumatic pathways integral with said tubular structure, each of said pathways extending from a distal port at said distal edge between adjacent protrusions to a proximal port at said proximal edge; and
   means for applying a negative pressure through said pneumatic pathways wherein the wall of the vessel lumen is drawn against said distal edge between said protrusions when said negative pressure is applied.

9. The apparatus of claim 8 wherein said means for applying a negative pressure comprises:
   a vacuum source;
   an annular attachment head configured to sealingly engage with said proximal edge of said tubular structure; and
   a plurality of vacuum tubes operatively connected between said vacuum source and said annular attachment head wherein each said vacuum tube is in pneumatic communication with a pneumatic pathway when said annular attachment head is in sealing engagement with said tubular structure.

10. The apparatus of claim 9 wherein said means for applying a negative pressure further comprises a handle operatively attached to said annular attachment head and having a vacuum actuator switch for controlling the application of negative pressure through said plurality of vacuum tubes.

11. The apparatus of claim 2 wherein said means for releasably engaging the wall of a vessel lumen comprises:
   a plurality of grasping members integral with said tubular structure, each of said grasping member comprising coacting jaws positioned at said distal edge between adjacent protrusions; and
   means for actuating said coacting jaws wherein the wall of the vessel lumen is grasped by said coacting jaws and compressed against said distal edge between said protrusions.

12. The apparatus of claim 2 wherein said means for releasably engaging the wall of a vessel lumen comprises:
   an elongated tube extending through the interior of said tubular structure and having proximal and distal ends;
   a tissue engaging member at the distal end of said elongated tube and positionable against the interior of the wall of the vessel lumen; and
   an actuator at the proximal end of said elongated tube for causing said tissue engaging member to engage the wall of the vessel lumen.

13. The apparatus of claim 12 wherein said tissue engaging member has an open and a closed position and forms a pointed tip when in said closed position.

14. The apparatus of claim 12 wherein said tissue engaging member comprises support members.

15. The apparatus of claim 12 wherein said tissue engaging member comprises an inflatable balloon, said elongated tube is in fluid communication with said balloon, and said actuator comprises a syringe for injecting fluid into said balloon.

16. The apparatus of claim 15 wherein said balloon is preshaped to conform to said protrusions.

17. The apparatus of 12 further comprising a rod slidably extending through said tube, said rod having proximal and distal ends, wherein said actuator is a rotatable knob, said distal end of said rod terminates in a pointed tip, and said proximal end of said rod is in threaded engagement with said rotatable knob, whereby rotation of said knob causes said rod to move axially through said tube.

18. The apparatus of claim 17 wherein said tissue engaging member comprises a radially expandable braided sheath.

19. The apparatus of claim 17 wherein said tissue engaging member comprises a plurality of deployable support members.

20. The apparatus of claim 2 further comprising a means for removing an annular needle from said annular needle passage.

21. The apparatus of claim 2 further comprising a cutting mechanism associated with said tubular structure for cutting an incision in the tissue wall.

22. An automatic suturing device comprising:

an outer tubular member having a distal edge forming a substantially sinusoidal configuration having peak sections and valley sections, said peak sections being distal relative to said valley sections and having an annular needle passage defined therein;

a plurality of disks rotationally mounted circumferentially within said outer tubular member wherein each of said disks is diametrically aligned with a peak section;

an inner tubular member coaxially positioned within said outer tubular member and rotationally engagable with said plurality of disks such that an annular needle operatively positioned within said annular needle passage is advanced through said passage by said rotational engagement; and means for releaseably engaging the wall of a vessel lumen against said distal edge of said outer tubular member whereby said tissue conforms to said substantially sinusoidal configuration.

23. The automatic suturing device of claim 22 wherein an annular needle is able to be advanced 360°.

24. The automatic suturing device of claim 22 further comprising a needle preloaded in a selected position within said annular needle passage.

25. The automatic suturing device of claim 22 wherein said substantially sinusoidal configuration comprises four, five, or six peak sections.

26. The automatic suturing device of claim 22 wherein each said peak section comprises an inwardly extending lip having an arcuate groove therein defining a portion of said annular needle passage.

27. The automatic suturing device of claim 22 further comprising means for removing an annular needle from said annular passage.

28. The automatic suturing device of claim 27 wherein said means for removing a needle comprises a radially disengageable peak section.

29. The automatic suturing device of claim 28 wherein said radially disengageable peak section comprises an inwardly extending notch and said inner tubular member comprises a circumferential groove for receiving said notch, said circumferential groove encircling slightly less than 360° and defining a contact point whereby said radially disengageable peak section radially disengages from said outer tubular section when said contact point is caused to engage said notch.

30. The automatic suturing device of claim 27 wherein said annular needle passage has a slightly helical configuration whereby the needle is advanced out of said passage after being advanced one revolution through said annular needle passage.

31. The automatic suturing device of claim 22 further comprising means for positioning said inner tubular member longitudinally within said outer tubular member wherein said inner tubular member engages said plurality of disks with an optimum amount of force to advance a needle through said annular needle passage.

32. The automatic suturing device of claim 22 for comprising means for rotating said inner tubular member whereby said inner tubular member rotationally engages said plurality of disks.

33. The automatic suturing device of claim 32 wherein said means for rotating comprises a knob attached to the proximal end of said inner tubular member.

34. The automatic suturing device of claim 22 wherein said plurality of disks comprise a deformable material for facilitating frictional engagement of a needle.

35. A method of automatically applying a purse string suture in the wall of a tissue structure comprising the steps of:

shaping the tissue wall into a substantially sinusoidal configuration having peak sections and valley sections; and passing an annular needle having a suture attached thereto in an annular path through said peak sections.

36. The method of claim 35 wherein said annular needle is passed through less than the thickness of the tissue wall.

37. The method of claim 35 wherein said step of shaping comprises providing a tubular structure at the suture site of the outer wall of the tissue structure, said tubular structure having a distal edge having a substantially sinusoidal configuration, and engaging the tissue wall against said distal edge whereby said tissue wall takes on said configuration of said distal edge.

38. The method of claim 37 wherein said tubular structure comprises a plurality of pneumatic pathways, each of said pathways extending from a distal port at said distal edge to a proximal port at the proximal end of said tubular structure, said step of shaping comprising applying a negative pressure through said pneumatic pathways whereby said tissue wall is suctioned against said distal edge.

39. The method of claim 38 wherein said tubular structure further comprises a plurality of grasping mechanisms, said step of engaging comprising grasping said tissue wall against said distal edge.

40. The method of claim 38 wherein said step of engaging comprises positioning an expandable member against the inner wall of the tissue structure and expanding said expandable member whereby said tissue wall conforms to said sinusoidal configuration.

41. The method of claim 40 wherein said expandable member comprises a balloon.

42. The method of claim 40 wherein said expandable member comprises a braided sheath.

43. The method of claim 40 further comprising the step of incising the tissue wall for introducing said expandable member within said tissue structure.

44. A method of automatically providing a purse string suture at a target site within the wall of a tissue structure comprising the steps of:

providing an annular structure having a distal edge comprising a substantially sinusoidal configuration;

engaging said distal edge against the target site;

conforming the tissue wall at the target site to said substantially sinusoidal configuration; and passing an annular needle through the tissue wall.

45. The method of claim 44 wherein said step of conforming the tissue wall comprises pulling up on the outer tissue wall at the target site.

46. The method of claim 44 wherein said step of conforming the tissue wall comprises pushing up on the inner tissue wall at the target site.

47. A method to create an annular suture in the wall of a target hollow vessel comprising:

contacting the target vessel with the distal end of a suture applier;

conforming the vessel wall to the distal end of the suture applier;

operating the suture applier to pass a needle attached to a suture in an annular path through the portions of the vessel that the that are conformed to the distal end of the suture applier.

* * * * *